United States Patent [19]

Yamamoto et al.

[11] 4,226,883
[45] Oct. 7, 1980

[54] CARBAMATE DERIVATIVES AND METHOD FOR MANUFACTURE THEREOF

[76] Inventors: Izuru Yamamoto, No. 5-1, Kamiyoga 2-chome, Setagaya-ku, Tokyo; Yohji Takahashi, No. 10-4, Ogawa 2-chome, Machida-shi, Tokyo; Nobuo Kyomura, No. 9-7, Mita 1-chome, Tama-ku, Kawasaki-shi, Kanagawa-ken, all of Japan

[21] Appl. No.: 921,750

[22] Filed: Jul. 3, 1978

Related U.S. Application Data

[62] Division of Ser. No. 622,413, Oct. 14, 1975.

[30] Foreign Application Priority Data

| Mar. 22, 1975 | [JP] | Japan | 50-34708 |
| Mar. 27, 1975 | [JP] | Japan | 50-37179 |
| Mar. 28, 1975 | [JP] | Japan | 50-37459 |
| Mar. 28, 1975 | [JP] | Japan | 50-37460 |
| Mar. 30, 1975 | [JP] | Japan | 50-38152 |
| Mar. 31, 1975 | [JP] | Japan | 50-38980 |
| Oct. 15, 1974 | [JP] | Japan | 49-118387 |
| Nov. 11, 1974 | [JP] | Japan | 49-129726 |
| Dec. 23, 1974 | [JP] | Japan | 49-147838 |
| Feb. 6, 1975 | [JP] | Japan | 50-15629 |
| Feb. 6, 1975 | [JP] | Japan | 50-15630 |
| Feb. 14, 1975 | [JP] | Japan | 50-18627 |

[51] Int. Cl.³ .................................... A01N 47/10
[52] U.S. Cl. .................................... 424/300
[58] Field of Search ............................. 424/700

[56] References Cited

U.S. PATENT DOCUMENTS

| 2,524,185 | 10/1950 | Zima et al. | 260/475 |
| 2,776,197 | 11/1957 | Gysin et al. | 71/2.4 |
| 2,955,070 | 10/1960 | Jones et al. | 424/300 |
| 3,062,865 | 11/1962 | Moore et al. | 424/300 |
| 3,215,595 | 11/1965 | Bocker et al. | 424/300 |
| 3,404,208 | 10/1968 | Robertson et al. | 424/300 |
| 3,639,616 | 2/1972 | Lichtman et al. | 424/300 |

FOREIGN PATENT DOCUMENTS

1128219  4/1962  Fed. Rep. of Germany.
2461129  7/1975  Fed. Rep. of Germany.

OTHER PUBLICATIONS

Hadaway, World Health Organ., 32, pp. 581–585 (1965).
Metclaf, J. Econ. Ent., 55, pp. 889–894.
Weiden, J., Agr. Food Chem., 13, pp. 200–204.
Kolbezen, J. Agr. Food Chem., 2, pp. 864–869.
Plapp, J. of Econ. Ent. 60, (43), pp. 1094–1102 (1967).
Yu, J. of Agr. Food Chem., vol. 20, pp. 537–540, (1972).

*Primary Examiner*—Allen J. Robinson
*Attorney, Agent, or Firm*—Stevens, Davis, Miller & Mosher

[57] ABSTRACT

Novel carbamate derivatives and a method for the manufacture thereof are disclosed. The carbamate derivatives or insecticidal compositions containing such carbamate derivatives as the active component exhibit an outstanding insecticidal effect on the organophosphorus or carbamate resistant green rice leafhoppers (*Nephotettix cincticeps* Uhler).

13 Claims, No Drawings

CARBAMATE DERIVATIVES AND METHOD FOR MANUFACTURE THEREOF

This is a division of application Ser. No. 622,413, filed Oct. 14, 1975.

FIELD OF THE INVENTION

The present invention relates to novel carbamate derivatives. More particularly, this invention relates to insecticidal carbamate derivatives represented by the general formula:

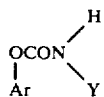  (I)

wherein, Ar denotes

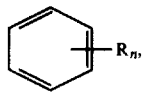

Y is alkyl or allyl having 2 to 6 carbon atoms, R is lower alkyl, lower alkoxy, lower alkenyloxy, lower alkinyloxy, lower alkylthio, lower alkylamino or lower alkenylamino and n is an integer having a value of 0 to 4.

DESCRIPTION OF THE PRIOR ART

Of the carbamate compounds represented by the general formula

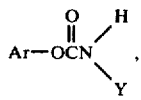

(wherein, Ar denotes a substituted phenyl group or naphthyl group), those which have heretofore been put to practical use as insecticides are limited to the carbamate compounds of the aforementioned formula wherein Y is methyl (hereinafter referred to as "methyl carbamates"). Said methyl carbamates have been extensively used as insecticides in rice fields. In recent years, they have shown a substantially reduced effect on green rice leafhoppers which are causing serious damage to rice crops in Japan. This is because green rice leafhoppers have acquired resistance to methyl carbamates. Owing to the appearance of such resistant green rice leafhoppers, it is now difficlt to effect perfect control of the insects by use of organophosphoric compounds or methyl carbamates. An acute need has been felt for the development of a new insecticide capable of manifesting a sufficient insecticidal effect on green rice leafhoppers which have acquired resistance to the conventional insecticides.

The term "resistance" as used herein means, as defined by WHO (World Health Organization), that a mass of insects has acquired an ability to withstand the action of a given insecticide used in a dosage rate enough to kill the majority of the insects in said mass.

The term "resistant strain" is used herein to mean a particular strain of insects which has acquired the aforementioned resistance to the insecticide.

BRIEF SUMMARY OF THE INVENTION

A primary object of the present invention is to provide novel carbamate compounds which exhibit an excellent insecticidal action on green rice leafhoppers having resistance to the conventional insecticides as described above. These carbamate compounds are represented by the general formula (I) mentioned above.

Another object of the present invention is to provide a method for the manufacture of said carbamate compounds.

Still another object of this invention is to provide insecticides containing said carbamate compounds as the active component.

In the course of a study continued with a view to accomplishing the objects described above, the inventors investigated the mechanism responsible for the appearance of green rice leafhoppers having resistance to methyl carbamates. The inventors found that the main factor for said resistance mechanism resides in the low sensitivity to methyl carbamate of the cholinesterase which is the target of carbamate. Based on this knowledge, the inventors made a search for a new carbamate compounds exhibited high anticholinesterase activity.

The inventors have consequently made a discovery that the carbamate compounds represented by the aforementioned general formula (I), namely the compounds of the formula wherein Y is propyl, ethyl or allyl each exhibit a specifically high activity to the restraint strain of green rice leafhoppers compared with methyl carbamates which have methyl as the substituent Y.

DETAILED DESCRIPTION OF THE INVENTION

The carbamate compounds according to the present invention are those which are represented by the aforementioned general formula (I). To be more specific, they are compounds of the general formula:

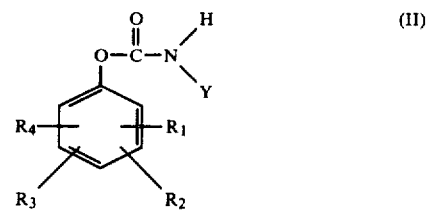 (II)

wherein, Y denotes alkyl or allyl having 2 to 6 carbon atoms, $R^1$, $R^2$, $R^3$ and $R^4$ are hydrogen or lower alkyl, lower alkoxy, lower alkenyloxy, lower alkinyloxy, lower alkylthio, lower alkylamino, lower alkenylamino or lower alkyl alkenyl amino, respectively. Specific examples of the carbamate compounds of the aforementioned description and their physical properties are collectively shown in Table 1. (Compounds marked with * throughout the specification are known methyl carbamates.)

Table 1

| Compounds | No. | Substituents Y | Physical properies (m.p. or $n_D$) | Molecular formula | C (%) | H (%) | N (%) | Halogen or S (%) |
|---|---|---|---|---|---|---|---|---|
| i-C₃H₇ (ortho) phenyl-O-C(=O)-NH-Y | 1* | CH₃ | m.p. 96°–97° C. | $C_{11}H_{15}NO_2$ =193.24 | 68.37 / 68.43 | 7.82 / 7.77 | 7.25 / 7.10 | |
| | 2 | C₂H₅ | m.p. 35°–38° C. | $C_{12}H_{17}NO_2$ =207.26 | 69.54 / 69.66 | 8.27 / 8.33 | 6.76 / 6.80 | |
| | 3 | nC₃H₇ | $n_D22$ 1.5030 | $C_{13}H_{19}NO_2$ =221.29 | 70.55 / 70.54 | 8.65 / 8.70 | 6.33 / 6.22 | |
| | 4 | nC₄H₉ | $n_D25$ 1.4960 | $C_{14}H_{21}NO_2$ =235.32 | 71.45 / 71.34 | 9.00 / 8.89 | 5.95 / 6.02 | |
| | 5 | CH₂CH=CH₂ | $n_D25$ 1.5137 | $C_{13}H_{17}NO_2$ =219.27 | 71.20 / 71.13 | 9.82 / 9.88 | 6.39 / 6.50 | |
| sec-C₄H₉ (ortho) | 6* | CH₃ | m.p. 28°–30° C. | $C_{12}H_{17}NO_2$ =207.26 | 69.54 / 69.40 | 8.27 / 8.30 | 6.76 / 6.84 | |
| | 7 | C₂H₅ | $n_D25$ 1.5041 | $C_{13}H_{19}NO_2$ =221.29 | 70.55 / 70.54 | 8.65 / 8.70 | 6.33 / 6.39 | |
| | 8 | nC₃H₇ | $n_D22$ 1.5016 | $C_{14}H_{21}NO_2$ =235.32 | 71.45 / 71.36 | 9.00 / 8.92 | 5.95 / 5.90 | |
| | 9 | nC₄H₉ | $n_D25$ 1.4985 | $C_{15}H_{23}NO_2$ =249.34 | 72.25 / 72.33 | 9.30 / 9.39 | 5.62 / 5.70 | |
| | 10 | —CH₂CH=CH₂ | $n_D25$ 1.5113 | $C_{14}H_{19}NO_2$ =233.30 | 72.07 / 72.17 | 8.21 / 8.11 | 6.00 / 6.08 | |
| i-C₃H₇ (meta) | 11* | CH₃ | m.p. 68°–69° C. | $C_{11}H_{15}NO_2$ =193.24 | 68.37 / 68.47 | 7.82 / 7.74 | 7.25 / 7.30 | |
| | 12 | C₂H₅ | $n_D24$ 1.5068 | $C_{12}H_{17}NO_2$ =207.26 | 69.54 / 69.49 | 8.27 / 8.20 | 6.76 / 6.80 | |
| | 13 | nC₃H₇ | $n_D24$ 1.5050 | $C_{13}H_{19}NO_2$ =221.29 | 70.55 / 70.60 | 8.65 / 8.54 | 6.33 / 6.21 | |
| | 14 | nC₄H₉ | $n_D24$ 1.5021 | $C_{14}H_{21}NO_2$ =235.32 | 71.45 / 71.38 | 9.00 / 8.97 | 5.95 / 6.02 | |
| sec-C₄H₉ (meta) | 15* | CH₃ | m.p. 46°–48° C. | $C_{12}H_{17}NO_2$ =207.26 | 69.54 / 69.59 | 8.27 / 8.33 | 6.76 / 6.86 | |
| | 16 | C₂H₅ | $n_D30$ 1.5028 | $C_{13}H_{19}NO_2$ =221.29 | 70.55 / 70.58 | 8.65 / 8.60 | 6.33 / 6.38 | |
| | 17 | nC₃H₇ | $n_D25$ 1.5115 | $C_{14}H_{21}NO_2$ =235.32 | 71.45 / 71.50 | 9.00 / 8.95 | 5.95 / 5.90 | |
| | 18 | n-C₄H₉ | $n_D30$ 1.4972 | $C_{15}H_{23}NO_2$ =249.34 | 72.25 / 72.30 | 9.30 / 9.34 | 5.62 / 5.68 | |
| sec-C₅H₁₁ (meta) | 19* | CH₃ | m.p. 38°–40° C. | $C_{13}H_{19}NO_2$ =221.29 | 70.55 / 70.54 | 8.65 / 8.72 | 6.33 / 6.38 | |
| | 20 | C₂H₅ | $n_D24$ 1.5160 | $C_{14}H_{21}NO_2$ =235.32 | 71.45 / 71.40 | 9.00 / 8.99 | 5.95 / 5.90 | |
| | 21 | nC₃H₇ | $n_D24$ 1.5023 | $C_{15}H_{23}NO_2$ =249.34 | 72.25 / 72.30 | 9.30 / 9.28 | 5.62 / 5.60 | |
| | 22 | C₄H₉ | $n_D24$ 1.4986 | $C_{16}H_{25}NO_2$ =262.98 | 72.96 / 72.02 | 9.57 / 9.60 | 5.32 / 5.30 | |
| | 23 | CH₂CH=CH₂ | $n_D20$ 1.5110 | $C_{15}H_{21}NO_2$ =247.33 | 72.84 / 72.66 | 8.56 / 8.78 | 5.66 / 5.86 | |
| CH₃ (meta) | 24* | CH₃ | m.p. 76°–77° C. | $C_9H_{11}NO_2$ =165.19 | 65.44 / 65.40 | 6.71 / 6.77 | 8.48 / 8.50 | |
| | 25 | C₂H₅ | m.p. 40°–42° C. | $C_{10}H_{13}NO_2$ =179.21 | 67.02 / 67.14 | 7.31 / 7.40 | 7.82 / 7.99 | |
| | 26 | n-C₃H₇ | m.p. 63°–64° C. | $C_{11}H_{15}NO_2$ =193.24 | 68.37 / 68.42 | 7.82 / 7.88 | 7.25 / 7.33 | |
| | 27 | n-C₄H₉ | m.p. 35° C. | $C_{12}H_{17}NO_2$ =207.26 | 69.54 / 69.70 | 8.27 / 8.09 | 6.76 / 6.68 | |
| | 28 | CH₂CH=CH₂ | $n_D30$ 1.5208 | $C_{11}H_{13}NO_2$ =191.22 | 69.09 / 69.18 | 6.85 / 6.94 | 7.33 / 7.23 | |
| C₂H₅ (meta) | 29* | CH₃ | m.p. 73.5°–74.5° C. | $C_{10}H_{13}NO_2$ =167.19 | 71.18 / 71.15 | 7.85 / 7.80 | 8.37 / 8.33 | |
| | 30 | C₂H₅ | $n_D19$ 1.5142 | $C_{11}H_{15}NO_2$ =193.24 | 68.37 / 68.55 | 7.82 / 7.91 | 7.25 / 7.14 | |
| | 31 | n-C₃H₇ | $n_D19$ 1.5029 | $C_{12}H_{17}NO_2$ =207.26 | 69.54 / 69.43 | 8.27 / 8.40 | 6.76 / 6.89 | |
| C₄H₉ (meta) | 32* | CH₃ | m.p. 144°–145° C. | $C_{13}H_{17}NO_2$ =207.26 | 69.54 / 69.70 | 8.27 / 8.18 | 6.76 / 6.80 | |
| | 33 | nC₃H₇ | m.p. 60°–62° C. | $C_{14}H_{21}NO_2$ =235.32 | 71.45 / 71.38 | 9.00 / 8.84 | 5.95 / 5.88 | |
| | 34 | CH₂CH=CH₂ | m.p. 66°–67° C. | $C_{14}H_{19}NO_2$ =233.30 | 72.07 / 72.01 | 8.21 / 8.11 | 6.00 / 5.89 | |

Table 1-continued

| Compounds | No. | Substituents Y | Physical properties (m.p. or $n_D$) | Molecular formula | Elemental Analysis C (%) | H (%) | N (%) | Halogen or S (%) |
|---|---|---|---|---|---|---|---|---|
| (3,4-dimethylphenyl carbamate) | 35* | $CH_3$ | m.p. 79°–80° C. | $C_{10}H_{13}NO_2$ =179.21 | 67.02 66.98 | 7.31 7.40 | 7.82 7.89 | |
| | 36 | $C_2H_5$ | m.p. 66°–67° C. | $C_{11}H_{15}NO_2$ =193.24 | 68.37 68.31 | 7.82 7.75 | 7.25 7.28 | |
| | 37 | $nC_3H_7$ | m.p. 58°–59° C. | $C_{12}H_{17}NO_2$ =207.26 | 69.54 69.70 | 8.27 8.33 | 6.76 6.79 | |
| | 38 | $n-C_4H_9$ | m.p. 62° C. | $C_{13}H_{19}NO_2$ =221.29 | 70.55 70.35 | 8.65 8.80 | 6.33 6.41 | |
| | 39 | $-CH_2CH=CH_2$ | m.p. 63°–65° C. | $C_{12}H_{15}NO_2$ =205.25 | 70.22 70.13 | 7.37 7.51 | 6.82 6.99 | |
| (3,5-dimethylphenyl carbamate) | 40* | $CH_3$ | m.p. 101°–102° C. | $C_{10}H_{13}NO_2$ =179.21 | 67.02 67.14 | 7.31 7.25 | 7.82 7.80 | |
| | 41 | $C_2H_5$ | m.p. 79°–81° C. | $C_{11}H_{15}NO_2$ =193.24 | 68.37 68.29 | 7.82 7.90 | 7.25 7.33 | |
| | 42 | $n-C_3H_7$ | m.p. 51°–52.5° C. | $C_{12}H_{17}NO_2$ =207.26 | 69.54 69.48 | 8.27 8.38 | 6.76 6.81 | |
| | 43 | $n-C_4H_9$ | m.p. 72°–74° C. | $C_{13}H_{19}NO_2$ =221.29 | 70.55 70.59 | 8.65 8.71 | 6.33 6.40 | |
| | 44 | $CH_2CH=CH_2$ | $n_D20$ 1.5236 | $C_{12}H_{15}NO_2$ =205.26 | 70.22 70.40 | 7.37 7.19 | 6.82 6.68 | |
| (3-methyl-5-isopropylphenyl carbamate) | 45* | $CH_3$ | m.p. 88°–90° C. | $C_{12}H_{17}NO_2$ =207.26 | 69.54 69.65 | 8.27 8.34 | 6.76 6.68 | |
| | 46 | $C_2H_5$ | m.p. 50°–51° C. | $C_{13}H_{19}NO_2$ =221.29 | 70.55 70.64 | 8.65 8.59 | 6.33 6.28 | |
| | 47 | $n-C_3H_7$ | $n_D20$ 1.5003 | $C_{14}H_{21}NO_2$ =235.32 | 71.45 71.31 | 9.00 9.11 | 5.95 5.84 | |
| | 48 | $n-C_4H_9$ | $n_D20$ 1.5020 | $C_{15}H_{23}NO_2$ =249.32 | 72.25 72.21 | 9.30 9.38 | 5.62 5.71 | |
| (1-naphthyl carbamate) | 49* | $CH_3$ | m.p. 142° C. | $C_{12}H_{11}NO_2$ =201.22 | 71.62 71.69 | 5.51 5.48 | 6.96 6.99 | |
| (3,4-diethylphenyl carbamate) | 50* | $CH_3$ | m.p. 69°–71° C. | $C_{12}H_{17}NO_2$ =207.26 | 69.54 69.44 | 8.27 8.41 | 6.76 6.60 | |
| | 51 | $n-C_3H_7$ | $n_D19.5$ 1.5050 | $C_{14}H_{21}NO_2$ =235.21 | 71.45 71.52 | 9.00 9.03 | 5.95 6.01 | |
| (3,5-diisopropylphenyl carbamate) | 52* | $CH_3$ | m.p. 80°–82° C. | $C_{14}H_{21}NO_2$ =235.21 | 71.45 71.33 | 9.00 8.81 | 5.95 5.79 | |
| | 53 | $n-C_3H_7$ | m.p. 43°–45° C. | $C_{16}H_{25}NO_2$ =262.98 | 72.96 72.84 | 9.57 9.65 | 5.32 5.31 | |
| (3,5-di-t-butylphenyl carbamate) | 54* | $CH_3$ | m.p. 106°–107.5° C. | $C_{16}H_{25}NO_2$ =262.98 | 72.96 73.09 | 9.57 9.48 | 5.32 5.40 | |
| | 55 | $n-C_3H_7$ | m.p. 68°–70° C. | $C_{18}H_{29}NO_2$ =291.42 | 74.18 74.22 | 10.03 10.03 | 4.81 4.76 | |
| | 56 | $-CH_2CH=CH_2$ | $n_D24.6$ 1.5060 | $C_{18}H_{27}NO_2$ =289.40 | 74.70 74.71 | 9.40 9.50 | 4.84 4.95 | |
| (2,3-dimethylphenyl carbamate) | 57* | $CH_3$ | m.p. 125°–126° C. | $C_{11}H_{15}NO_2$ =193.24 | 68.37 68.25 | 7.82 7.73 | 7.25 7.40 | |
| | 58 | $n-C_3H_7$ | m.p. 40°–41° C. | $C_{13}H_{19}NO_2$ =221.29 | 70.55 70.60 | 8.65 8.71 | 6.33 6.21 | |

Table 1-continued

| Compounds | No. | Substituents Y | Physical properts (m.p. or $n_D$) | Molecular formula | Elemental Analysis C (%) | H (%) | N (%) | Halogen or S (%) |
|---|---|---|---|---|---|---|---|---|
| [structure: 2,4-dimethylphenyl carbamate] | 59* | CH$_3$ | m.p. 110°–112° C. | C$_{11}$H$_{15}$NO$_2$ =193.24 | 68.37 68.44 | 7.82 7.88 | 7.25 7.20 | |
| | 60 | n-C$_3$H$_7$ | m.p. 56°–58° C. | C$_{13}$H$_{19}$NO$_2$ =221.29 | 70.55 70.62 | 8.65 8.78 | 6.33 6.31 | |
| [structure: 2,6-dimethyl-4-methylphenyl carbamate] | 61* | CH$_3$ | m.p. 139°–140° C. | C$_{11}$H$_{15}$NO$_2$ =193.24 | 68.37 68.33 | 7.82 7.96 | 7.25 7.36 | |
| | 62 | n-C$_3$H$_7$ | m.p. 80°–81° C. | C$_{13}$H$_{19}$NO$_2$ =221.29 | 70.55 70.65 | 8.65 8.72 | 6.33 6.26 | |
| [structure: 3,4,5-trimethylphenyl carbamate] | 63* | CH$_3$ | m.p. 114°–115° C. | C$_{11}$H$_{15}$NO$_2$ =193.24 | 68.37 68.50 | 7.82 7.69 | 7.25 7.29 | |
| | 64 | n-C$_3$H$_7$ | m.p. 94°–96° C. | C$_{13}$H$_{19}$NO$_2$ =221.29 | 70.55 70.71 | 8.65 8.71 | 6.33 6.31 | |
| [structure: 2-isopropyl-4,5-dimethylphenyl carbamate] | 65* | CH$_3$ | m.p. 102°–103° C. | C$_{13}$H$_{19}$NO$_2$ =221.29 | 70.55 70.71 | 8.65 8.66 | 6.33 6.50 | |
| | 66 | n-C$_3$H$_7$ | $n_D$ 1.5039 | C$_{15}$H$_{23}$NO$_2$ =249.34 | 72.25 72.33 | 9.30 9.30 | 5.62 5.58 | |
| [structure: 2-methyl-4-isopropyl-5-methylphenyl carbamate] | 67* | CH$_3$ | m.p. 111°–112° C. | C$_{13}$H$_{19}$NO$_2$ =221.29 | 70.55 70.51 | 8.65 8.77 | 6.33 6.40 | |
| | 68 | n-C$_3$H$_7$ | $n_D$ 1.5081 | C$_{15}$H$_{23}$NO$_2$ =249.34 | 72.25 72.31 | 9.30 9.44 | 5.62 5.54 | |
| [structure: 2-t-butyl-4,6-dimethylphenyl carbamate] | 69* | CH$_3$ | m.p. 101.5°–102.5° C. | C$_{14}$H$_{21}$NO$_2$ =235.21 | 71.45 71.56 | 9.00 8.92 | 5.95 6.11 | |
| | 70 | n-C$_3$H$_7$ | m.p. 77°–83° C. | C$_{16}$H$_{25}$NO$_2$ =262.98 | 72.96 73.08 | 9.57 9.62 | 5.32 5.20 | |
| [structure: 2,3-dimethyl-5-t-butylphenyl carbamate] | 71* | CH$_3$ | m.p. 141°–143° C. | C$_{14}$H$_{21}$NO$_2$ =235.21 | 71.45 71.45 | 9.00 8.83 | 5.95 6.00 | |
| | 72 | n-C$_3$H$_7$ | m.p. 89°–91° C. | C$_{16}$H$_{25}$NO$_2$ =262.98 | 72.96 72.89 | 9.57 9.65 | 5.32 5.30 | |

Table 1-continued

| Compounds | No. | Substituents Y | Physical properts (m.p. or $n_D$) | Molecular formula | Elemental Analysis C (%) | H (%) | N (%) | Halogen or S (%) |
|---|---|---|---|---|---|---|---|---|
| 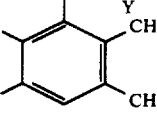 | 73* | CH$_3$ | m.p. 178°–179° C. | C$_{12}$H$_{17}$NO$_2$ =207.26 | 69.54 69.70 | 8.27 8.40 | 6.76 6.60 | |
| | 74 | n-C$_3$H$_7$ | m.p. 115°–117° C. | C$_{14}$H$_{21}$NO$_2$ =235.21 | 71.45 71.52 | 9.00 8.89 | 5.95 5.80 | |
| 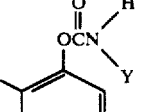 | 75* | CH$_3$ | m.p. 90° C. | C$_8$H$_8$ClNO$_2$ =185.61 | 51.76 51.60 | 4.34 4.45 | 7.55 7.53 | 19.10 19.33 |
| 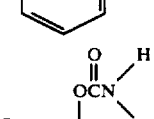 | 76* | CH$_3$ | m.p. 85°–87° C. | C$_9$H$_{11}$NO$_3$ =181.19 | 59.66 59.75 | 6.12 6.30 | 7.73 7.84 | |
| | 77 | n-C$_3$H$_7$ | $n_D20$ 1.5238 | C$_{11}$H$_{15}$NO$_3$ =209.24 | 63.14 63.25 | 7.23 7.36 | 6.69 6.62 | |
| | 78 | n-C$_4$H$_9$ | $n_D24.6$ 1.5155 | C$_{12}$H$_{17}$NO$_3$ 223.26 | 64.55 64.59 | 7.68 7.75 | 6.27 6.28 | |
| 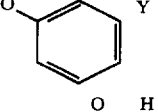 | 79* | CH$_3$ | m.p. 81°–83° C. | C$_{10}$H$_{13}$NO$_3$ =195.21 | 61.52 61.62 | 6.71 6.90 | 7.18 7.22 | |
| | 80 | n-C$_3$H$_7$ | m.p. 51°–52° C. | C$_{12}$H$_{17}$NO$_3$ =223.26 | 64.55 64.72 | 7.68 7.83 | 6.27 6.38 | |
| 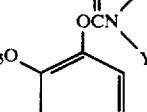 | 81* | CH$_3$ | m.p. 91° C. | C$_{11}$H$_{15}$NO$_3$ =209.24 | 63.14 63.20 | 7.23 7.10 | 6.69 6.83 | |
| | 82 | C$_2$H$_5$ | m.p. 54°–56.5° C. | C$_{12}$H$_{17}$NO$_3$ =223.26 | 64.55 64.61 | 7.68 7.83 | 6.27 6.33 | |
| | 83 | n-C$_3$H$_7$ | m.p. 44° C. | C$_{13}$H$_{19}$NO$_3$ =237.29 | 65.80 65.95 | 8.07 8.23 | 5.90 5.98 | |
| | 84 | n-C$_4$H$_9$ | $n_O21.5$ 1.5012 | C$_{14}$H$_{21}$NO$_3$ =251.32 | 66.90 66.78 | 8.42 8.29 | 5.57 5.49 | |
| | 85 | —CH$_2$CH=CH$_2$ | $n_O20$ 1.5362 | C$_{13}$H$_{17}$NO$_3$ =235.27 | 66.36 66.51 | 7.28 7.35 | 5.95 6.01 | |
| 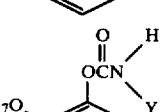 | 86* | CH$_3$ | m.p. 60°–61° C. | C$_{12}$H$_{17}$NO$_3$ =223.26 | 64.55 64.38 | 7.68 7.70 | 6.27 6.40 | |
| | 87 | n-C$_3$H$_7$ | $n_D23$ 1.4879 | C$_{14}$H$_{21}$NO$_3$ =251.32 | 66.90 67.08 | 8.42 8.55 | 5.57 5.53 | |
| 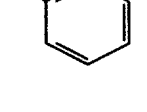 | 88* | CH$_3$ | m.p. 40°–41° C. | C$_{11}$H$_{13}$NO$_3$ =207.22 | 63.75 63.88 | 6.32 6.45 | 6.76 6.65 | |
| | 89 | n-C$_3$H$_7$ | m.p. 37°–38° C. | C$_{13}$H$_{17}$NO$_3$ =235.27 | 66.36 66.52 | 7.28 7.40 | 5.95 5.86 | |
| 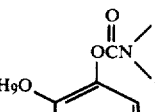 | 90* | CH$_3$ | m.p. 80.5°–82° C. | C$_{11}$H$_{11}$NO$_3$ =205.21 | 64.38 64.50 | 5.40 5.52 | 6.83 6.93 | |
| | 91 | n-C$_3$H$_7$ | m.p. 63°–4° C. | C$_{13}$H$_{15}$NO$_3$ =233.26 | 66.93 66.81 | 6.48 6.40 | 6.01 6.08 | |
| 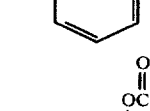 | 92* | CH$_3$ | m.p. 56° C. | C$_{10}$H$_{13}$NO$_3$ =195.21 | 61.52 61.65 | 6.71 6.86 | 7.18 7.25 | |
| | 93 | C$_2$H$_5$ | $n_D23$ 1.5165 | C$_{11}$H$_{15}$NO$_3$ =209.24 | 63.14 63.32 | 7.23 7.40 | 6.69 6.55 | |
| | 94 | n-C$_3$H$_7$ | $n_D23$ 1.5112 | C$_{12}$H$_{17}$NO$_3$ =223.26 | 64.55 64.73 | 7.68 7.70 | 6.27 6.38 | |
| | 95 | n-C$_4$H$_9$ | $n_D23$ 1.5110 | C$_{13}$H$_{19}$NO$_3$ =237.29 | 65.80 65.69 | 8.07 8.04 | 5.90 5.82 | |

Table 1-continued

| Compounds | No. | Substituents Y | Physical properts (m.p. or n_D) | Molecular formula | C (%) | H (%) | N (%) | Halogen or S (%) |
|---|---|---|---|---|---|---|---|---|
| 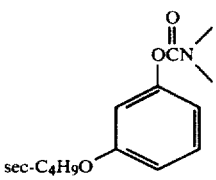 sec-C₄H₉O― | 96* | CH₃ | $n_D{23}$ 1.5010 | $C_{12}H_{17}NO_3$ =223.26 | 64.55 64.40 | 7.68 7.53 | 6.27 6.34 | |
| | 97 | n-C₃H₇ | m.p. 60°-62° C. | $C_{14}H_{21}NO_3$ =251.32 | 66.90 66.74 | 8.42 8.39 | 5.57 5.66 | |
| 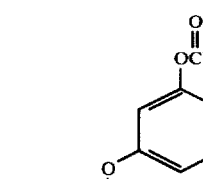 CH₂=CH―CH₂ | 98* | CH₃ | m.p. 57.5°-58.5° C. | $C_{11}H_{13}NO_3$ =207.22 | 63.75 63.82 | 6.32 6.41 | 6.76 6.60 | |
| | 99 | n-C₃H₇ | $n_D{23}$ 1.5243 | $C_{13}H_{17}NO_3$ =235.27 | 66.36 66.51 | 7.28 7.38 | 5.95 6.03 | |
| 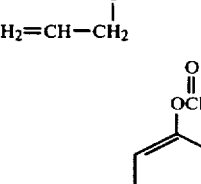 CH≡C―CH₂ | 100* | CH₃ | m.p. 80.5°-82.0° C. | $C_{11}H_{11}NO_3$ =205.21 | 64.38 64.52 | 5.40 5.62 | 6.83 6.77 | |
| | 101 | n-C₃H₇ | m.p. 51°-5° C. | $C_{13}H_{15}NO_3$ =233.26 | 66.93 66.84 | 6.48 6.58 | 6.01 5.97 | |
| 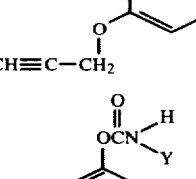 SCH₃ | 102* | CH₃ | m.p. 75°-76° C. | $C_9H_{11}NO_2S$ =197.25 | 54.80 54.63 | 5.62 5.70 | 7.10 6.96 | 16.26 16.35 |
| | 103 | C₂H₅ | m.p. 70° C. | $C_{10}H_{13}NO_2S$ =211.28 | 56.85 56.72 | 6.20 6.22 | 6.63 6.80 | 15.18 15.29 |
| | 104 | n-C₃H₇ | m.p. 73°-74° C. | $C_{11}H_{15}NO_2S$ =225.30 | 58.64 58.60 | 6.71 6.58 | 6.22 6.25 | 14.23 14.35 |
| | 105 | n-C₄H₉ | m.p. 56° C. | $C_{12}H_{17}NO_2S$ =239.33 | 60.22 60.35 | 7.16 7.28 | 5.85 5.82 | 13.40 13.19 |
| 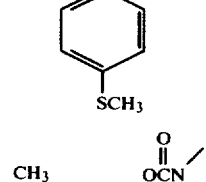 | 106* | CH₃ | m.p. 73°-75° C. | $C_{10}H_{14}N_2O_2$ =194.23 | 61.83 61.95 | 7.27 7.40 | 14.42 14.45 | |
| | 107 | n-C₃H₇ | $n_D{20}$ 1.5324 | $C_{12}H_{18}N_2O_2$ =222.28 | 64.84 64.98 | 8.16 8.32 | 12.60 12.55 | |
| 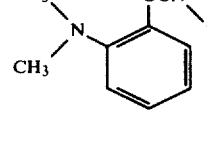 | 108* | CH₃ | m.p. 53°-55° C. | $C_{14}H_{18}N_2O_2$ =246.30 | 68.27 68.38 | 7.37 7.42 | 11.37 11.48 | |
| | 109 | n-C₃H₇ | m.p. 44°-45° C. | $C_{16}H_{22}N_2O_2$ =274.35 | 70.04 70.21 | 8.08 8.25 | 10.21 10.34 | |
| 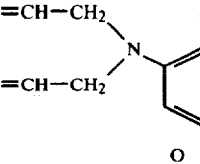 | 110* | CH₃ | m.p. 70°-72° C. | $C_{11}H_{16}N_2O_2$ =208.25 | 63.44 63.60 | 7.74 7.70 | 13.45 13.51 | |
| | 111 | n-C₃H₇ | m.p. 55°-56° C. | $C_{13}H_{20}N_2O_2$ =236.31 | 66.07 66.18 | 8.53 8.72 | 11.86 11.95 | |
| 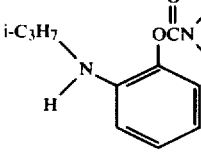 | 112* | CH₃ | m.p. 85°-86° C. | $C_{10}H_{14}N_2O_2$ =194.23 | 61.83 68.72 | 7.27 8.16 | 14.42 12.71 | |
| | 113 | n-C₃H₇ | m.p. 43°-44° C. | $C_{12}H_{18}N_2O_2$ =222.28 | 68.84 | 8.16 | 12.60 | |
| | 114 | n-C₄H₉ | m.p. 69°-70° C. | $C_{13}H_{20}N_2O_2$ =236.31 | 66.07 66.25 | 8.53 8.69 | 11.86 11.83 | |
| | 115 | n-C₆H₁₃ | m.p. 39°-40° C. | $C_{15}H_{24}N_2O_2$ =264.36 | 68.15 68.28 | 9.15 9.28 | 10.60 10.55 | |

Table 1-continued

| Compounds | No. | Substituents Y | Physical properts (m.p. or $n_D$) | Molecular formula | Elemental Analysis C (%) | H (%) | N (%) | Halogen or S (%) |
|---|---|---|---|---|---|---|---|---|
| (structure with $C_2H_5$, $C_2H_5$ on N, meta to OC(O)NHY on benzene) | 116* | $CH_3$ | m.p. 85.5°–90° C. | $C_{12}H_{18}N_2O_2$ =222.28 | 64.84 64.70 | 8.16 8.09 | 12.60 12.76 | |
| | 117 | n-$C_3H_7$ | $n_D18$ 1.5307 | $C_{14}H_{22}N_2O_2$ =250.33 | 67.17 67.31 | 8.86 8.94 | 11.19 11.25 | |
| (structure with 3,5-di-CH$_3$, 4-N(CH$_3$)$_2$ phenyl) | 118* | $CH_3$ | m.p. 83°–85° C. | $C_{12}H_{18}N_2O_2$ =222.28 | 64.84 64.80 | 8.16 8.30 | 12.60 12.53 | |
| | 119 | $C_2H_5$ | m.p. 75°–76° C. | $C_{13}H_{20}N_2O_2$ =236.31 | 66.07 66.25 | 8.53 8.69 | 11.86 11.95 | |
| | 120 | n-$C_3H_7$ | m.p. 55°–56° C. | $C_{14}H_{22}N_2O_2$ =250.33 | 67.17 67.38 | 8.86 9.02 | 11.19 11.07 | |
| | 121 | n-$C_4H_9$ | m.p. 39°–40° C. | $C_{15}H_{24}N_2O_2$ =264.36 | 68.15 68.28 | 9.15 9.30 | 10.60 10.54 | |
| | 122 | —$CH_2CH=CH_2$ | $n_D24.6$ 1.5273 | $C_{14}H_{20}N_2O_2$ =248.32 | 67.71 67.58 | 8.12 8.09 | 11.28 11.28 | |
| (structure with 3,5-di-CH$_3$, 4-N($C_2H_5$)$_2$ phenyl) | 123* | $CH_3$ | m.p. 62°–63° C. | $C_{14}H_{22}N_2O_2$ =250.33 | 67.17 67.31 | 8.86 8.97 | 11.19 11.23 | |
| | 124 | n-$C_3H_7$ | $n_D21.5$ 1.5122 | $C_{16}H_{26}N_2O_2$ =278.38 | 69.03 68.87 | 9.41 9.45 | 10.06 9.93 | |
| | 125 | —$CH_2CH=CH_2$ | $n_D20$ 1.5228 | $C_{16}H_{24}N_2O_2$ =276.37 | 69.53 69.46 | 8.75 8.60 | 10.14 10.27 | |
| (structure with 3,5-di-CH$_3$, 4-N(CH$_2$CH=CH$_2$)$_2$ phenyl) | 126* | $CH_3$ | m.p. 61°–62° C. | $C_{16}H_{22}N_2O_2$ =274.35 | 70.04 70.10 | 8.08 8.20 | 10.21 10.08 | |
| | 127 | $C_2H_5$ | m.p. 39°–41° C. | $C_{17}H_{24}N_2O_2$ =288.38 | 70.80 70.88 | 8.39 8.55 | 9.71 9.96 | |
| | 128 | n-$C_3H_7$ | $n_D19$ 1.5250 | $C_{18}H_{26}N_2O_2$ =302.20 | 71.49 71.57 | 8.67 8.78 | 9.26 9.28 | |
| | 129 | n-$C_4H_9$ | $n_D19$ 1.5217 | $C_{19}H_{28}N_2O_2$ =316.43 | 72.11 72.34 | 8.92 9.09 | 8.85 8.94 | |
| | 130 | —$CH_2CH=CH_2$ | $n_D24.6$ 1.5340 | $C_{18}H_{24}N_2O_2$ =300.39 | 71.97 72.10 | 8.05 8.20 | 9.33 9.40 | |
| (structure with 3,5-di-CH$_3$, 4-N(CH$_3$)(CH$_2$CH=CH$_2$) phenyl) | 131* | $CH_3$ | m.p. 55°–57° C. | $C_{14}H_{20}N_2O_2$ =248.32 | 67.71 68.01 | 8.12 8.00 | 11.28 11.12 | |
| | 132 | n-$C_3H_7$ | $n_D14.5$ 1.5237 | $C_{16}H_{24}N_2O_2$ =276.37 | 69.53 69.69 | 8.75 8.67 | 10.14 10.27 | |
| (structure with sec-$C_4H_9$, $OCH_3$ on phenyl) | 133* | $CH_3$ | m.p. 69.5°–71° C. | $C_{13}H_{19}NO_3$ =237.29 | 65.80 66.03 | 8.07 7.89 | 5.90 5.88 | |
| | 134 | n-$C_3H_7$ | m.p. 43.5°–45° C. | $C_{15}H_{23}NO_3$ | 67.89 67.78 | 8.74 8.68 | 5.28 5.39 | |
| (structure with $CH_3$, $SCH_3$ on phenyl) | 135* | $CH_3$ | m.p. 73°–75° C. | $C_{10}H_{13}NO_2S$ =211.28 | 56.85 56.93 | 6.20 6.11 | 6.63 6.79 | 15.18 15.30 |
| | 136 | n-$C_3H_7$ | m.p. 44°–46° C. | $C_{12}H_{17}NO_2S$ =239.33 | 60.22 60.10 | 7.16 7.22 | 5.85 5.71 | 13.40 13.29 |
| | 137 | —$CH_2CH=CH_2$ | m.p. 56° C. | $C_{12}H_{15}NO_2S$ =237.31 | 60.78 60.83 | 6.37 6.20 | 5.90 5.88 | 13.51 13.36 |

Table 1-continued

| Compounds | No. | Substituents Y | Physical propert s (m.p. or n_D) | Molecular formula | Elemental Analysis C (%) | H (%) | N (%) | Halogen or S (%) |
|---|---|---|---|---|---|---|---|---|
| 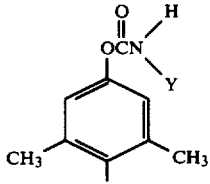 | 138* | CH₃ | m.p. 118°–129° C. | $C_{11}H_{15}NO_2S$ =225.30 | 58.64 58.49 | 6.71 6.88 | 6.22 6.23 | 14.23 14.38 |
| | 139 | n-C₃H₇ | m.p. 64°–65° C. | $C_{13}H_{19}NO_2S$ =253.35 | 61.62 61.74 | 7.56 7.47 | 5.53 5.60 | 12.66 12.40 |
| 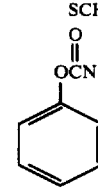 | 140* | CH₃ | m.p. 83°–84° C. | $C_8H_9NO_2$ =151.16 | 63.56 63.63 | 6.00 6.11 | 9.27 9.33 | |
| | 141 | C₂H₅ | m.p. 48° C. | $C_9H_{11}NO_2$ =165.19 | 65.44 65.40 | 6.71 6.83 | 8.48 8.52 | |
| | 142 | n-C₃H₇ | m.p. 55°–56° C. | $C_{10}H_{13}NO_2$ =179.21 | 67.02 67.00 | 7.31 7.18 | 7.82 7.76 | |
| | 143 | n-C₄H₉ | m.p. 41° C. | $C_{11}H_{15}NO_2$ =193.24 | 68.37 68.30 | 7.82 7.90 | 7.25 7.33 | |
| | 144 | —CH₂CH=CH₂ | m.p. 29°–30° C. | $C_{10}H_{11}NO_2$ =177.20 | 67.78 67.82 | 6.26 6.30 | 7.91 7.85 | |

Of the carbamate compounds shown in Table 1, the following exhibit a high insecticidal activity on resistant green rice leafhoppers:
2-isopropylpheny-N-ethylcarbamate,
2-isopropylphenyl-N-n-propylcarbamate,
2-isopropylphenyl-N-allylcarbamate,
2-sec-butylphenyl-N-ethylcarbamate,
2-sec-butylphenyl-N-n-propylcarbamate,
2-sec-butylphenyl-N-allylcarbamate,
3-isopropylphenyl-N-n-propylcarbamate,
3-sec-butylphenyl-N-n-propylcarbamate,
3-sec-amylphenyl-N-n-propylcarbamate,
3-methylphenyl-N-ethylcarbamate,
3-methylphenyl-N-n-propylcarbamate,
3-methylphenyl-N-allylcarbamate,
3-ethylphenyl-N-n-propylcarbamate,
3-tert-butylphenyl-N-n-propylcarbamate,
3,4-dimethylphenyl-N-ethylcarbamate,
3,4-dimethylphenyl-N-n-propylcarbamate,
3,4-dimethylphenyl-N-allylcarbamate,
3.5-dimethylphenyl-N-ethylcarbamate,
3,5-dimethylphenhl-N-n-propylcarbamate,
3,5-dimethylphenyl-N-allylcarbamate,
3-methyl-5-isopropylphenyl-N-ethylcarbamate,
3-methyl-5-isopropylphenyl-N-n-propylcarbamate,
3,4-diethylphenyl-N-n-propylcarbamate,
3,5-di-isopropylphenyl-N-n-propylcarbamate,
3,5-di-tert-butylphenyl-N-n-propylcarbamate,
2,3,5-trimethylphenyl-N-n-propylcarbamate,
2,4,5-trimethylphenyl-N-n-propylcarbamate,
2,4,6-trimethylphenyl-N-n-propylcarbamate,
3,4,5-trimethylphenyl-N-n-propylcarbamate,
2-isopropyl-4,5-dimethylphenyl-N-n-propylcarbamate,
2,5-dimethyl-4-isopropylphenyl-N-n-propylcarbamate,
2,4-dimethyl-6-tert-butylphenyl-N-n-propylcarbamate,
2,3-dimethyl-5-tert-butylphenyl-N-n-propylcarbamate,
2,3,5,6-tetramethylphenyl-N-n-propylcarbamate,
2-methoxyphenyl-N-n-propylcarbamate,
2-ethoxyphenyl-N-n-propylcarbamate,
2-isopropoxyphenyl-N-ethylcarbamate,
2-isopropoxyphenyl-N-n-propylcarbamate
2-isopropoxyphenyl-N-allylcarbamate,
2-sec-butoxyphenyl-N-n-propylcarbamate,
2-allyloxyphenyl-N-n-propylcarbamate,
2-propynyloxyphenyl-N-n-propylcarbamate,
3-ethoxyphenyl-N-n-propylcarbamate,
3-sec-butoxyphenyl-N-n-propylcarbamate,
3-allyloxyphenyl-N-n-propylcarbamate,
3-propynyloxyphenyl-N-n-propylcarbamate,
4-methylthiophenyl-N-n-propylcarbamate,
2-dimethylaminophenyl-N-n-propylcarbamate,
2-diallylaminophenyl-N-n-propylcarbamate,
2-isopropylaminophenyl-N-n-propylcarbamate,
3-dimethylaminophenyl-N-n-propylcarbamate,
3-diethylaminopheny-N-n-propylcarbamate
3,5-dimethyl-4-dimethylaminophenyl-N-ethylcarbamate,
3,5-dimethyl-4-dimethylaminophenyl-N-n-propylcarbamate,
3,5-dimethyl-4-dimethylaminophenyl-N-allylcarbamate,
3,5-dimethyl-4-diethylaminophenyl-N-n-propylcarbamate
3,5-dimethyl-4-diethylaminophenyl-N-allylcarbamate,
3,5-dimethyl-4-diallylaminophenyl-N-ethylcarbamate,
3,5-dimethyl-4-diallylaminophenyl-N-n-propylcarbamate,
3,5-dimethyl-4-diallylaminophenyl-N-allylcarbamate,
3,5-dimethyl-4-methyl-allylaminophenyl-N-n-propylcarbamate,
3-sec-butyl-4-methoxyphenyl-N-n-propylcarbamate,
3-methyl-4-methylthiophenyl-N-n-propylcarbamate,
3-methyl-4-methylthiophenyl-N-allylcarbamate,
3,5-dimethyl-4-methylthiophenyl-N-n-propylcarbamate,
phenyl-N-ethylcarbamate,
phenyl-N-n-propylcarbamate,
phenyl-N-allylcarbamate,
Of the above mentioned carbamate compounds, the following exhibit low mammalian toxicity as well as high insecticidal activity:
3-methylphenyl-N-n-propylcarbamate
2-isopropylphenyl-N-n-propylcarbamate
2-sec-butylphenyl-N-n-propylcarbamate
3,5-dimethylphenyl-N-n-propylcarbamate
3,4-dimethylphenyl-N-n-propylcarbamate
3-isopropylphenyl-N-n-propylcarbamate
3-isobutylphenyl-N-n-propylcarbamate
3-tert butylphenyl-N-n-propylcarbamate
3-methyl-5-isopropylphenyl-N-n-propylcarbamate The carbamate compounds of the present invention described above are prepared by various methods. Of the various methods available for this purpose, the most advantageous are described.

(a) The preparation can be effected by the reaction of phenols represented by the general formula:

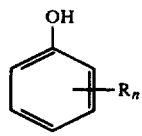
(III)

(wherein, R and n are as defined in the aforementioned general formula (I) with isocyanates or carbamoyl chlorides represented by the general formulas:

$$\text{YNCO} \quad \text{(IV) or}$$
(V)

(wherein Y denotes an alkyl or allyl having 2 to 6 carbon atoms).

(b) The preparation can otherwise be effected by the reaction of alkyl chloroformate-substituted phenyl esters represented by the general formula:

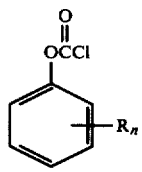
(VI)

(wherein, R and n are as defined in the aforementioned general formula (I)) with a primary amine represented by the general formula $YNH_2$ (wherein, Y denotes an alkyl or allyl having 2 to 6 carbon atoms).

When an isocyanate is used in the method (a) described above, the manufacture is accomplished by allowing an alkyl-substituted phenol of the aforementioned general formula (III) to react with an isocyanate (IV) in slightly excess amounts generally from 1 to 1.2 moles per mole, in an inert solvent or in the absence of a solvent. Examples of the inert solvents which are suitable are aromatic hydrocarbons such as benzene, toluene, and xylene and ethers such as diethyl ether and dioxane. The reaction temperature is generally in the range of from 0° to 150° C., although it may be varied over a fairly wide range. This reaction is accelerated by addition to the reaction system of a tertiary amine such as triethyl amine or a tin compound such as the tin salt of dioctoic acid or di-n-butyl tin dilaurate, for example.

When carbamoyl chloride is used in the method (a), the manufacture is accomplished by using the carbamoyl chloride (V) in an equivalent weight or a slightly excess amount based on the phenol (III).

The reaction (a) or (b) described above may be carried out without a solvent. It is generally desirable, however, that the reaction be carried out in the presence of a suitable solvent.

For example, an aromatic hydrocarbon such as benzene or toluene, an ether such as diethyl ether or dioxane or water can be used.

The reaction is generally carried out at room temperature or a lower temperature. Usually it is selected from the range of from 0° to 25° C. Upon occasion, however, the reaction may be carried out at a suitably elevated temperature. The reaction can be continued at room temperature or a lower temperature and, as the reaction nears termination, be performed at a slightly elevated temperature so as to be brought to completion.

As hydrochloric acid is formed in the course of the reaction, an inorganic or organic basic substance such as, for example, sodium hydrogen carbonate, potassium carbonate, sodium hydroxide, triethyl amine or pyridine is added.

Alternatively, pyridine or quinoline may be used to serve simultaneously as the solvent for the reaction and as a sequestering agent for the hydrochloric acid.

The method of the reaction (b) described above is effected by causing an alkyl chloroformate-substituted phenyl ester of the general formula (VI) obtained by the reaction of phosgene upon a corresponding alkyl-substituted phenol to react with an amine with or without a solvent such as, for example, water, an ether or benzene. Although the reaction temperature is not critically limited, a slow reaction is obtained at temperatures below 10° C., while if the reaction temperature is elevated too much above the level of 40° C., possible losses of the raw material and the reaction product are encountered.

It is, therefore, generally proper to select a reaction temperature in the range of from 20° to 40° C. Normally, an appropriate amount of amine is in the range of from 2.2 to 2.4 moles per mole of chloroformate which is being reacted with the amine.

Of the total amount of the amine, the amount in excess of the equivalent amount consumed in the reaction with the chloroformate is included for the purpose of sequestering the hydrochloric cid which is formed in the course of the reaction. For this purpose, such excess may be substituted with a strong alkali such as sodium hydroxide.

According to the method of this invention, a variety of carbamates such as are enumerated in Table 1 above can be manufactured. Additionally, the following can likewise be manufactured 2-methylphenyl carbamate, 2-ethylphenyl carbamate, 2-tertiary-butylphenyl carbamate, 4-methylphenyl carbamate, 2,3-dimethylphenyl carbamate, 2,4-dimethylphenyl carbamate, 2,5-dimethylphenyl carbamate, 2,6-dimethylphenyl carbamate, 3,5-di-(tertiary butyl)-phenyl carbamate, 3-methyl-4-isopropylphenyl carbamate, 3-methyl-5-tertiarybutyl phenyl carbamate, 3,5-di-(isopropyl)-phenyl carbamate, etc. Some of the N-lower alkyl (or alkenyl) carbamates of the present invention exhibit, by themselves, an insecticidal activity to a fairly high extent and, when used in combination with conventionally known methyl carbamates, manifest a notably high insecticidal activity. Other N-lower alkyl (or alkenyl) carbamates of the present invention, even if they fail to exhibit any effective insecticidal activity by themselves, manifest an outstanding insecticidal activity when they are used in conjunction with such known methyl carbamates. In such a combined application, they act quite effectively upon the sensitive strain and resistant strain of green rice leafhoppers. A composition which has at least two carbamate compounds combined as described above manifests not a mere additive effect but a powerful synergistic effect against green rice leafhoppers. The insecticidal composition containing, as the active component thereof, the carbamate compound of the present invention, therefore, provides a stable powerful insecticidal activity on sensitive green rice leafhoppers (S), resistant green rice leafhoppers (R) and green rice leafhoppers of the strain which has acquired a markedly developed degree of resistance (RN).

It has also been confirmed that the carbamate compounds of the aforementioned general formula (II), when used in combination with known organophosphoric insecticides, manifest a high insecticidal activity even on various insects (such as, for example, rice stem borers (*Chilo suppressalis* Walker), green rice leafhoppers, smaller brown leafhoppers (*Laodelphax striatellus* Fallén), root aphides (*Rhopalosiphum rufiabdominalis* Sasaki, *Aneocia fulviabdominalis* Sasaki, *Tetraneura nigriabdominalis* Sasaki, etc.), tobacco cutworms (*Prodenia litura* Fabricius), spider mites (various species of family Tetranychidae), smaller tea tortrices (*Adoxophyes orand* Fischer von Ruml/o/ slerstamm) and hygienic pests including houseflies and mosquitos) which are now posing a serious problem by developing resistance to organophosphoric preparations.

The effect of a composition containing both the carbamate compound of an present invention and the organophosphoric compound is not a mere additive effect but a powerful synergistic insecticidal effect. Thus, the use of this composition offers an advantage of additively enlarging the insecticidal spectrum of each of the components making up that composition. The insecticidal activity manifested by this composition is extremely effective to resistant insects. Insecticidal compositions according to the present invention can include a carbamate compound of the present invention and known N-methyl carbamates. For example, those N-methyl carbamate compounds enumerated in Table 2-1 are useful for this purpose.

Table 2-1

| N-methylcarbamate | Common name |
| --- | --- |
| 1-naphthyl-N-methylcarbamate | NAC |
| 2-isopropylphenyl-N-methylcarbamate | MIPC |
| 2-sec-butylphenyl-N-methylcarbamate | BPMC |
| 3-methylphenyl-N-methylcarbamate | MTMC |
| 3-isopropylphenyl-N-methylcarbamate | |
| 3-sec-butylphenyl-N-methylcarbamate | |
| 3-sec-amylphenyl-N-methylcarbamate | |
| 3-tert-butylphenyl-N-methylcarbamate | TBPC |
| 3,4-dimethylphenyl-N-methylcarbamate | MPMC |
| 3,5-dimethylphenyl-N-methylcarbamate | XMC |
| 3-methyl-5-isopropylphenyl-N-methylcarbamate | Promecarb |
| 2,3,5-trimethylphenyl-N-methylcarbamate | |
| m-(1-methylbutyl)phenyl-N-methylcarbamate | |
| 3,4,5-trimethylphenyl-N-methylcarbamate | |
| m-(1-ethylpropyl)phenyl-N-methylcarbamate | |
| 4-ethylthiophenyl-N-methylcarbamate | |
| 2-isopropoxyphenyl-N-methylcarbamate | PHC |
| 2-chloro-4,5-dimethylphenyl-N-methylcarbamate | |
| 2-chlorophenyl-N-methylcarbamate | CPMC |
| 4-methylthio-3,5-dimethyl-N-methylcarbamate | methiocarb |
| 4-diallylamino-3,5-dimethylphenyl-N-methylcarbamate | APC |
| 4-dimethylamino-3-methyl-N-methylcarbamate | Aminocarb |
| 4-dimethylamino-3,5-dimethylphenyl-N-methylcarbamate | Zectran ® (DOW Chemical) |
| 2,3-dihydro-2,2-dimethyl-benzofuran-7-yl-N-methylcarbamate | Carbofuran |
| 2,3-isopropylidenedioxyphenyl-N-methylcarbamate | Bendiocarb |
| 2-dimethylcarbamoyl-3-methyl-5-pyrazolyl dimethylcarbamate | dimetilan |
| 2-(1,3-dioxolan-2-yl) phenyl-N-methylcarbamate | dioxacarb |
| 3-dimethylaminomethyleneiminophenyl-N-methylcarbamate | formetanate |
| 1-(methylthio)ethylideneamino-N-methylcarbamate | methomyl |
| 2-methyl-2-(methylthio)propionaldehydro-O-(methylcarbamoyl)oxime | aldicarb |
| 1-(2-cyanoethylthio)ethylideneamino methylcarbamate | thiocarboxime |

(®: trade mark)

These N-methyl carbamate compounds may be used combined, in the form of a mixture of two or more members, with the carbamate compounds of the present invention. Examples of the possible mixtures for such compositions are as shown in Table 2-2.

Table 2-2

| 3-methylphenyl-N-n-propylcarbamate | + 3-methylphenyl-N-methylcarbamate |
| --- | --- |
| " | + 3,4-dimethylphenyl-N-methylcarbamate |
| " | + 3,5-dimethylphenyl-N-methylcarbamate |
| " | + 2-sec-butylphenyl-N-methylcarbamate |
| " | + 1-naphthyl-N-methylcarbamate |
| " | + 2-isopropoxyphenyl-N-methylcarbamate |
| " | + 2-isopropylphenyl-N-methylcarbamate |
| " | + 3,5-dimethyl-4-dimethylaminophenyl-N-methylcarbamate |
| " | + 4-diallylamino-3,5-dimethylphenyl-N-methylcarbamate |
| " | + 1-(methylthio)ethylideneamino-N-methylcarbamate |
| " | + 2,3-dihydro-2,2-dimethyl-benzofuran-7-yl-N-methylcarbamate (carbofuran) |

Table 2-2-continued

| | |
|---|---|
| | + 4-dimethylamino-3-methylphenyl-N-methylcarbamate |
| 3,4-dimethyl-N-n-propylcarbamate | |
| | + 3-methylphenyl-N-methylcarbamate |
| " | + 3,4-dimethylphenyl-N-methylcarbamate |
| " | + 3,5-dimethylphenyl-N-methylcarbamate |
| " | + 2-sec-butylphenyl-N-methylcarbamate |
| " | + 1-naphthyl-N-methylcarbamate |
| " | + 2-isopropoxyphenyl-N-methylcarbamate |
| " | + 2-isopropylphenyl-N-methylcarbamate |
| " | + 3,5-dimethyl-4-dimethylaminophenyl-N-methylcarbamate |
| " | + 4-diallylamino-3,5-dimethylphenyl-N-methylcarbamate |
| " | + 1-(methylthio)-ethylideneamino-N-methylcarbamate |
| " | + 2,3-dihydro-2,2-dimethyl-benzofuran-7-yl-N-methylcarbamate |
| " | 4-dimethylamino-3-methylphenyl-N-methylcarbamate |
| 3,5-dimethylphenyl-N-n-propylcarbamate | |
| | + 3-methylphenyl-N-methylcarbamate |
| " | + 3,4-dimethylphenyl-N-methylcarbamate |
| " | + 3,5-dimethylphenyl-N-methylcarbamate |
| " | + 2-sec-butylphenyl-N-methylcarbamate |
| " | + 1-naphthyl-N-methylcarbamate |
| " | + 2-isopropoxyphenyl-N-methylcarbamate |
| " | + 2-isopropylphenyl-N-methylcarbamate |
| " | + 3,5-dimethyl-4-dimethylaminophenyl-N-methylcarbamate |
| 3-sec-amylphenyl-N-n-propylcarbamate | |
| | + 3-methylphenyl-N-methylcarbamate |
| | + 3,4-dimethylphenyl-N-methylcarbamate |
| 3-sec-amylphenyl-N-n-propylcarbamate | |
| " | + 3,5-dimethylphenyl-N-methylcarbamate |
| " | + 2-sec-butylphenyl-N-methylcarbamate |
| " | + 1-naphthyl-N-methylcarbamate |
| " | + 2-isopropoxyphenyl-N-methylcarbamate |
| " | + 2-isopropylphenyl-N-methylcarbamate |
| 2-isopropylphenyl-N-n-propylcarbamate | |
| | + 3-methylphenyl-N-methylcarbamate |
| " | + 3,4-dimethylphenyl-N-methylcarbamate |
| " | + 3,5-dimethylphenyl-N-methylcarbamate |
| " | + 2-sec-butylphenyl-N-methylcarbamate |
| " | + 1-naphthyl-N-methylcarbamate |
| " | + 2-isopropoxyphenyl-N-methylcarbamate |
| " | + 2-isopropylphenyl-N-methylcarbamate |
| 2-sec-butylphenyl-N-n-propylcarbamate | |
| | + 3-methylphenyl-N-methylcarbamate |
| " | + 3,4-dimethylphenyl-N-methylcarbamate |
| " | + 3,5-dimethylphenyl-N-methylcarbamate |
| " | + 2-sec-butylphenyl-N-methylcarbamate |
| " | + 1-naphthyl-N-methylcarbamate |
| " | + 2-isopropoxyphenyl-N-methylcarbamate |
| " | + 2-isopropylphenyl-N-methylcarbamate |

2-isopropylphenyl-N-n-propylcarbamate + 2-isopropylphenyl-N-ethylcarbamate + 2-isopropylphenyl-N-methylcarbamate 2-sec-butylphenyl-N-methylcarbamate + 1-naphthyl-N-methylcarbamate + 3-methylphenyl-N-n-propylcarbamate 2-isopropylphenyl-N-n-butylcarbamate + 2-isopropylphenyl-N-n-propylcarbamate + 2-isopropylphenyl-N-ethylcarbamate + 2-isopropylphenyl-N-methylcarbamate 3-methylphenyl-N-n-propylcarbamate + 3-methylphenyl-N-methylcarbamate + S-[1,2-bis(ethoxycarbonyl)ethyl] dimethyl-phosphorothiolothionate (malathion ®)

3-methylphenyl-N-n-propylcarbamate + 3-methylphenyl-N-methylcarbamate + diethyl 2-isopropyl-4-methyl-6-pyrimidinylphosphorothionate (diazinon ®)

3,4-dimethylphenyl-N-n-propylcarbamate + 3-methylphenyl-N-methylcarbamate + S-[1,2-bis(ethoxycarbonyl)ethyl] dimethyl-phosphorothiolthionate (malathion ®)

3,4-dimethylphenyl-N-n-propylcarbamate + 3,4-dimethylphenyl-N-methylcarbamate + 2-isopropyl-4-methyl-6-pyrimidinyl-phosphoro-thionate (diazinon ®)

Further, the specific carbamate compounds represented by the general formula (II) can be used in the form of a mixture of two or more members in a manner similar to the use of N-methyl carbamate compounds.

Examples of the organophosphoric insecticides which are useful as additive components in the insecticidal compositions are cited in Table 3.

Table 3

S-[1,2-bis(ethoxycarbonyl)ethyl]dimethyl phosphorothiolothionate (Malathion ®; American Cyanamid Co.),
dimethyl 4-nitro-m-tolyl phosphorothionate (MFP),
S-[α-(ethoxycarbonyl)benzyl]dimethyl phosphorothiolothionate (PAP),
dimethyl 4-methylthio-m-tolyl phosphorothionate (MPP),
diethyl 2-isopropyl-6-methyl-4-pyrimidinyl phosphorothionate (Diazinon ®; Nippon kayaku Co., Ltd.),
O, S-dimethyl N-acetylphosphoramidothioate (Ortran ®; Hokko Chemical Industry Co., Ltd.),
dipropyl p-methylthiophenyl phosphate (Kayaphos ®; Nippon kayaku Co., Ltd.),
diethyl 2,3-dihydro-3-oxo-2-phenyl-6-pyridazinyl phosphorothionate (Ofnuck ®; Mitsui toatsu Chemical, Inc.),
diethyl S-methylcarbarbamoylmethyl phosphorothiolothionate (dimethoate),
2-chloro-1-(2,4,5-trichlorophenyl)vinyl dimethyl phosphate (CVMP),
S-benzyl diisopropyl phosphorothiolate (IBP),
2-bromo-2,5-dichlorophenyl methyl phenylphosphorothionate (MBCP),
S-2 acetamidoethyl dimethyl phosphorothiolothionate (DAEP),
diethyl S-(2-ethylthioethyl)phosphorothiolothionate (ethylthiometon),
dimethyl S-2-(1-methylcarbamoylethylthio)ethyl phosphorothiolate (vamidothion)
S-p-chlorophenyl dimethyl phosphorothiolate (DMCP)
diethyl 2,2,2-trichloro-1-hydroxyethylphosphonate (DEP)
2,2-dichlorovinyl dimethyl phosphate (DDVP)
2-chloro-1-(2,4-dichlorophenyl)vinyl diethyl phosphate (CVP)
2-methoxy 4H-1,3,2-benzodioxaphosphorin-2-sulfide (salithion)
p-cyanophenyl dimethyl phosphorothionate (CYAP)
p-cyanophenyl ethyl phenylphosphonothionate (CYP)
dimethyl 4-nitrophenyl phosphorothionate (parathion-methyl),
diethyl 4-nitrophenyl phosphorothionate (parathion),
O,O-diethyl O-(3,5,6-trichloro-2-pyridyl)phosphorothioate (chlorpyrifos),
diethyl S-(ethylthiomethyl)phosphorothiolthioate (phorate),
O-ethyl phenyl ethylphosphonothiolothionate (fonofos),
S-(3,4-dihydro-4-oxobenzo[a]-[1,2,3]-triazin-3-ylmethyl)dimethyl phosphorothiolothionate (azinphosmethyl),
dimethyl-1-methyl-2-methyl-carbamoyl-vinyl phosphate (monocrotophos),
S-(2,3-dihydro-5-methoxy-2-oxo-1,3,4-thiaziazol-3-ylmethyl)dimethyl phosphorothiolothionate (methidathion), ( ):common name
®:trade mark Generally the ratio in which the N-methyl carbamate compound and the specific N-lower alkyl (or alkenyl) carbamate compound of the present invention are used is in the range of 1 : 0.2 – 5. The highest cooperative activity is manifested when the mixing ratio is in the range of 1 : 0.5 – 2.

The ratio in which the carbamate compound of the present invention represented by the general formula (II) and the organophosphoric insecticidal compound is generally appropriate in the range of 1 : 0.2 – 5. The dosage rate of this composition is in the range of from 100 to 300 g, computed as active components per 10 ares.

When the carbamate compound of the present invention is actually used as an agricultural insecticide, it is generally mixed with a carrier and adjuvants and then prepared in the form of emulsion, wettable agent, dust, fine granule or pellets so as to ensure effective dispersion of the active components throughout the surface of a field of application.

It may also be used in the form of a mixture with other active components such as insecticides, fungicides, miticides, herbicides, cooperating agents and fertilizers which have no possibility of inhibiting the activity of the active components thereof. To be more specific, examples of liquid carriers which are suitable include water, alcohols, ketones, ethers, aliphatic hydrocarbons, aromatic hydrocarbons, halogenated hydrocarbons, acid amides, esters and nitriles. They may be used in the form of a mixture of two or more members.

Examples of suitable solid carriers are clay kaolin, bentonite, talc, silica and diatomaceous earth. They also may be used in the form of a mixture of two or more members.

Examples of adjuvants which are usable for this purpose include emulsifiers, dispersants, extenders and other surface active agents such as nonionic surface active agents (polyoxyethylene alkylaryl ethers, polyoxyethylene sorbitan monolaurate, etc.), cationic surface active agents (alkyldimethylbenzyl ammonium chlorides, alkylpyridinium chlorides, etc.), anionic surface active agents (alkylbenzene sulfonates, lignosulfonates, higher alcohol sulfates, etc.) and amphoteric surface active agents (alkyldimethyl betaines, dodecylaminoethyl glycin, etc.). They may be used either alone or in the form of a mixture of two or more members.

The insecticidal activities which the carbamate compounds of the present invention and the insecticidal composition containing said compounds as the active components exhibit upon resistant green rice leafhoppers will be described more specifically below with reference to test examples and preferred embodiments. The present invention is not limited to these preferred embodiments and test examples but permit modifications which do not depart from the spirit of the invention.

In the test examples and the preferred embodiments, where the compound Nos. are mentioned, they correspond to the compound Nos. indicated in Table 1 and where "parts" are mentioned, they are parts by weight.

PREPARATION OF COMPOUND (CARBAMATE)

Example 1

A quantity 10.8 g (0.1 mol) of m-cresol was heated to 90° C. and thereby melted and 0.3 g of dioctylic tin acid as a catalyst was added thereto. While the resultant mixture was continuously agitated, 8.9 g (0.105 mol) of n-propyl isocyanate was introduced dropwise very gradually.

After the completion of the dropwise introduction, the reaction product was cooled to solidify and then recrystallized from n-hexane. Consequently, there was obtained 17.4 g of 3-methylphenyl-N-propylcarbamate in the form of colorless crystals having a melting point of 63°-64° C.

The yield was found to be 90% (Compound No. 26).

Example 2

In 150 ml of anhydrous benzene, 12.2 g (0.1 mol) of 3,4-dimethyl phenol was dissolved. To the resultant solution were added 9.4 g (0.11 mol) of n-propyl isocyanate and five drops of triethyl amine. The mixture was left to stand overnight. On the following day, the mixture was distilled under reduced pressure to remove benzene therefrom. The distillation residue was recrystallized from n-hexane. Consequently there was obtained 17.6 g of 3,4-dimethylphenyl-N-n-propylcarbamate in the form of colorless crystals having a melting point of 58°-59° C.

The yield was found to be 85% (Compound No. 37).

Example 3

In 150 ml of anhydrous ether, 12.2 g (0.1 mol) of 3,5-dimethyl phenol was dissolved. To the resultant solution were added 9.1 g (0.11 mol) of allyl isocyanate and five drops of triethyl amine. The mixture was heated under reflux for 5 hours and then distilled to remove ether. The yellowish brown oily distillation residue was purified by means of a column chromatographic system packed with 1 kg of silica gel (with a mixed solvent of n-hexane and ether used as the eluting agent). Consequently there was obtained 19.1 g of 3,5-dimethylphenyl-N-allylcarbamate in the form of a yellow liquid having a refractive index $n_D^{20}$ = 1.5236 (20° C.). The yield was found to be 93% (Compound No. 44).

Example 4

In 100 ml of anhydrous benzene, 14.8 g (0.1 mol) of 2-allyl-5-methyl phenol was dissolved. While the solution was continuously agitated at room temperature, 9.4 g (0.11 mol) of n-propyl isocyanate and five drops of triethyl amine were added. The mixture thus formed was allowed to stand overnight. When the mixture was distilled under reduced pressure to remove the solvent therefrom, there was obtained 23 g of a light yellow oily substance. This substance was purified by means of a chromatographic column packed with silica gel to produce 19.5 g of 2-allyl-5-methylphenyl-N-n-propyl carbamate in the form of a liquid, having a refractive index of $n_D^{20.5}$ = 1.5166.

The yield was found to be 83%.

EXAMPLE 5

In 100 ml of anhydrous benzene, 20.6 g of 3,5-di-t-butyl phenol was dissolved. While the resultant solution was continuously agitated at room temperature, 9.4 g (0.11 mol) of n-propyl isocyanate and several drops of triethyl amine were added thereto. After eight hours of agitation at 50° to 60° C., the mixture was distilled under reduced pressure to remove the solvent therefrom. Consequently there was obtained a crude product in the form of a colorless solid. This solid was recrystallized from n-hexane and there was obtained 25 g of 3,5-di-t-butylphenyl-N-n-propylcarbamate in the form of colorless needles having a melting point of 68°-70° C. The yield was found to be 86% (compound No. 55).

Example 6

In 50 ml of pyridine, 10.8 g (0.1 mol) of m-cresol was dissolved. While the resultant solution was continuously agitated at 10° C., 14.6 g (0.12 mol) of N-n-propyl carbamoyl chloride was introduced dropwise and the resultant mixture was left to stand overnight at room temperature. Then, the mixture was poured into ice water and subsequently 150 ml of ether was added thereto. The ether layer was washed with 2N hydrochloric acid, an aqueous 5% potassium carbonate solution and water in the order mentioned, dried with Glauber's salt and distilled to remove the ether therefrom under atmospheric pressure. The residue was recrystallized from n-hexane. Consequently there was obtained 16.0 g of 3-methylphenyl-N-n-propylcarbamate in the form of colorless crystals having a melting point of 63°-64° C. The yield was found to be 83% (Compound No. 26).

Example 7

In 100 ml of benzene, 17.0 g (0.1 mol) of chloroformic acid-3-methylphenyl ester was dissolved. While the resultant solution was held at 30° C. under continued agitation, 13.2 g (0.22 mol) of n-propyl amine was gradually introduced. The resultant mixture was left to stand overnight. Then it was transferred into ice water. The precipitated n-propyl amine hydrochloride was dissolved. Then the benzene layer was separated, washed first with dilute hydrochloric acid, then with a dilute aqueous solution of sodium hydroxide and finally with water. The benzene layer was dried over anhydrous sodium sulfate and distilled under reduced pressure to remove the benzene therefrom. When the residue was recrystallized from n-hexane, there was obtained 16.4 g of 3-methylphenyl-N-n-propylcarbamate in the form of colorless crystals having a melting point of 63°-64° C. The yield was found to be 85% (Compound No. 26). cl PREPARATION OF COMPOUND (INSECTICIDE)

Example 1: (Dust)

A dust is obtained by uniformly mixing and pulverizing 2 parts of Compound No. 13 and 98 parts of talc.

Example 2: (Dust)

A dust is obtained by uniformly mixing and pulverizing 2 parts of Compound No. 17 and 98 parts of clay.

Example 3: (Dust)

A dust is obtained by uniformly mixing and pulverizing 2 parts of Compound No. 21 and 98 parts of clay.

EXAMPLE 4: (Fine Granule)

A fine granular insecticide is obtained by uniformly mixing 3 parts of Compound No. 50, 2 parts of sodium alkylbenzene sulfonate and 95 parts of talc with water in a speed kneader (made by Showa Engineering, Ltd.) to form granules and subsequently breaking the granules to an optimum particle diameter by means of a speed mill (made by Showa Engineering, Ltd.).

Example 5: (Wettable Powder)

A wettable powder is obtained by uniformly mixing and pulverizing 50 parts of Compound No. 51, 3 parts of Sorpol CT-1 (surface active agent made by Toho Chemical Industry Co., Ltd.) and 47 parts of a mixture of talc and bentonite.

Example 6: (Emulsion)

An emulsion is obtained by dissolving 30 parts of Compound No. 53 and 3 parts of sodium alkylbenzene sulfonate in a mixture of 37 parts of dimethyl formamide and 30 parts of xylene.

Test Example 1

A. Inhibition of Cholinesterase (ChE)

The activity of ChE was performed by the acethyethiocholine method [Ellman (1961), Biochemical Pharmacology 7: 88–95].

(1) Enzyme Preparation: 30 green rice leafhopper females, *Nephotettix cincticeps*, were homogenized with 20 ml of phosphate buffer (1/15 M, pH 7.4) and solubilized by sonication (20 KHz, 10 min.). After centrifuged (30,000 g, 10 min.), the supernatant was used as the source of ChE.

(2) Inhibition: 1.0 ml of enzyme solution was incubated with 0.1 ml of inhibitor which diluted with acetone at 30° C. for 30 min. ((2) solution).

(3) Determination of ChE activity: 1.0 ml of acetylthiochline ($3.5/2 \times 10^{-2}$M), 1.0 ml of DTNB (5,5′-dithiobis-2-nitrobenzoic acid, $2.5 \times 10^{-4}$M) and 4.0 ml of phosphate buffer (1/15 M, pH 7.4) were added to the (2) solution and incubated at 30° C. for 10 min. After incubation, 1.0 mol of eserine ($2 \times 10^{-3}$M) was added in order to stop the enzyme reaction and the optical density of the yellow solution was measured at 412 m$\mu$ on the spectrophotometer.

B: Insecticidal Test (1) A 20-mg portion of a given test compound was weighed out and dissolved in 10 ml of acetone. The resultant solution was diluted at proper times with acetone.

(2) With a micro-syringe, the acetone solution of the test compound was topically applied to the thoracic region of female green rice leafhoppers at a fixed dose of 0.2 $\mu$l per head.

(3) The female green rice leafhoppers thus treated were placed in a plastic cup prepared in advance (measuring 7 cm in diameter and 3.5 cm in depth and containing rice seeds) and kept at a constant temperature of $26 \pm 1°$ C. After 24 hours' standing, the dead insects were counted.

In the case of a mixed insecticide, the $LD_{50}$ was shown as a total dosage. The co-toxicity coefficient was obtained by the method of Sun and Johnson (1960) (J. Econ. Ertomol. 53: 887–892). When the value determined by this method is 1 or over, synergistic action is present.

The test results were as shown in Table 4 (for individual insecticides) and Table 5 (for mixtures).

Table 4

| Compound No. | Inhibition of Cholinesterase $I_{50}$ (M) (1) | | | Insecticidal Activity (after 24 hrs.) $LD_{50}$ ($\mu$g/g) (2) | | |
|---|---|---|---|---|---|---|
| | S (3) | R (4) | R/S (5) | S (3) | R (4) | R/S (5) |
| 1.* | $1.3 \times 10^{-6}$ | $1.2 \times 10^{-4}$ | 92.3 | 3.6 | 82.8 | 23.0 |
| 2. | $3.2 \times 10^{-5}$ | $5.2 \times 10^{-5}$ | 1.6 | 28.0 | 59.1 | 2.1 |
| 3. | $1.3 \times 10^{-4}$ | $4.7 \times 10^{-5}$ | 0.4 | 50.0 | 65.8 | 1.3 |
| 4. | $>10^{-3}$ | $8.6 \times 10^{-5}$ | <0.09 | >100.0 | >100.0 | — |
| 5. | $2.6 \times 10^{-5}$ | $2.2 \times 10^{-5}$ | 0.8 | 10.6 | 32.6 | 3.1 |
| 6.* | $1.1 \times 10^{-6}$ | $8.3 \times 10^{-5}$ | 75.5 | 2.7 | 76.6 | 28.4 |
| 7. | $2.5 \times 10^{-5}$ | $4.4 \times 10^{-5}$ | 1.8 | 14.2 | 37.5 | 2.6 |
| 8. | $1.2 \times 10^{-4}$ | $3.3 \times 10^{-5}$ | 0.8 | 56.1 | 65.8 | 1.2 |
| 9. | $>10^{-3}$ | $1.4 \times 10^{-4}$ | <0.1 | >100.0 | 100.0 | <1.0 |
| 10. | $1.7 \times 10^{-5}$ | $1.9 \times 10^{-5}$ | 1.1 | 9.9 | 42.6 | 4.3 |
| 11.* | $5.4 \times 10^{-7}$ | $5.8 \times 10^{-6}$ | 10.7 | 1.4 | 27.6 | 21.1 |
| 12. | $3.7 \times 10^{-5}$ | $1.7 \times 10^{-5}$ | 0.5 | 8.6 | 31.5 | 3.7 |
| 13. | $3.3 \times 10^{-5}$ | $4.7 \times 10^{-6}$ | 0.1 | 17.7 | 25.6 | 1.4 |
| 14. | $7.4 \times 10^{-5}$ | $1.7 \times 10^{-5}$ | 0.2 | >100.0 | >100.0 | — |
| 15.* | $9.8 \times 10^{-8}$ | $4.3 \times 10^{-6}$ | 54.3 | 0.8 | 15.3 | 19.0 |
| 16. | $6.5 \times 10^{-6}$ | $5.6 \times 10^{-6}$ | 0.9 | 5.4 | 20.1 | 3.7 |
| 17. | $1.3 \times 10^{-5}$ | $3.2 \times 10^{-6}$ | 0.2 | 10.2 | 12.5 | 1.2 |
| 18. | $5.0 \times 10^{-5}$ | $4.3 \times 10^{-6}$ | 0.09 | 33.2 | 31.5 | 0.9 |
| 19.* | $5.7 \times 10^{-8}$ | $1.4 \times 10^{-6}$ | 24.6 | 1.6 | 14.8 | 9.3 |
| 20. | $3.4 \times 10^{-6}$ | $4.1 \times 10^{-6}$ | 1.2 | 19.0 | 28.0 | 1.5 |
| 21. | $7.2 \times 10^{-6}$ | $1.1 \times 10^{-6}$ | 0.2 | 7.0 | 20.4 | 2.9 |
| 22. | $5.1 \times 10^{-5}$ | $6.3 \times 10^{-6}$ | 0.1 | 40.6 | 35.4 | 0.9 |
| 23. | $4.2 \times 10^{-6}$ | $1.3 \times 10^{-6}$ | 0.3 | 21.3 | 15.3 | 0.7 |
| 24.* | $6.5 \times 10^{-6}$ | $1.3 \times 10^{-4}$ | 20.0 | 4.0 | 39.4 | 9.9 |
| 25. | $3.4 \times 10^{-4}$ | $1.8 \times 10^{-4}$ | 0.5 | 12.3 | 45.2 | 3.7 |
| 26. | $2.9 \times 10^{-4}$ | $4.8 \times 10^{-5}$ | 0.2 | 81.8 | 51.2 | 0.6 |
| 27. | $>10^{-3}$ | $2.7 \times 10^{-4}$ | <0.3 | >100.0 | >100.0 | — |
| 28. | $2.2 \times 10^{-4}$ | $2.1 \times 10^{-4}$ | 1.0 | 46.7 | 85.2 | 1.8 |
| 29.* | $2.9 \times 10^{-6}$ | $1.2 \times 10^{-4}$ | 41.4 | 2.7 | 40.3 | 14.9 |
| 30. | $2.0 \times 10^{-4}$ | $1.6 \times 10^{-4}$ | 0.8 | 51.3 | 85.2 | 1.7 |
| 31. | $1.5 \times 10^{-4}$ | $3.9 \times 10^{-5}$ | 0.3 | 54.0 | 29.4 | 0.5 |
| 32.* | $7.2 \times 10^{-7}$ | $1.2 \times 10^{-5}$ | 16.6 | 1.6 | 50.0 | 31.3 |
| 33. | $2.2 \times 10^{-5}$ | $5.1 \times 10^{-6}$ | 0.2 | 30.6 | 45.1 | 1.5 |
| 34. | $2.6 \times 10^{-5}$ | $8.9 \times 10^{-6}$ | 0.3 | 35.4 | 38.0 | 1.1 |
| 35.* | $2.8 \times 10^{-6}$ | $6.4 \times 10^{-5}$ | 22.9 | 4.5 | 21.3 | 4.7 |
| 36. | $1.4 \times 10^{-4}$ | $7.6 \times 10^{-5}$ | 0.5 | 21.8 | 71.3 | 3.3 |

Table 4-continued

| | | | | | | |
|---|---|---|---|---|---|---|
| 37. | $1.9 \times 10^{-4}$ | $1.4 \times 10^{-5}$ | 0.07 | 36.2 | 29.4 | 0.8 |
| 38. | $5.6 \times 10^{-4}$ | $2.0 \times 10^{-5}$ | 0.04 | >100.0 | >100.0 | — |
| 39. | $5.7 \times 10^{-5}$ | $1.6 \times 10^{-5}$ | 0.3 | 32.9 | 25.0 | 0.8 |
| 40.* | $4.2 \times 10^{-6}$ | $7.5 \times 10^{-5}$ | 17.9 | 4.7 | 25.0 | 5.3 |
| 41. | $1.1 \times 10^{-4}$ | $7.9 \times 10^{-5}$ | 0.7 | 38.4 | 76.6 | 2.0 |
| 42. | $2.2 \times 10^{-4}$ | $1.2 \times 10^{-5}$ | 0.05 | 48.1 | 35.4 | 0.7 |
| 43. | $6.8 \times 10^{-4}$ | $2.7 \times 10^{-5}$ | 0.04 | >100.0 | >100.0 | — |
| 44. | $5.7 \times 10^{-5}$ | $2.2 \times 10^{-5}$ | 0.4 | 72.4 | 65.3 | 0.9 |
| 45.* | $1.2 \times 10^{-6}$ | $1.4 \times 10^{-5}$ | 11.6 | 3.4 | 39.6 | 11.6 |
| 46. | $4.6 \times 10^{-5}$ | $2.3 \times 10^{-5}$ | 0.5 | 54.0 | 50.0 | 0.9 |
| 47. | $4.5 \times 10^{-5}$ | $8.5 \times 10^{-6}$ | 0.1 | 25.0 | 35.4 | 1.4 |
| 48. | $>10^{-3}$ | $8.8 \times 10^{-5}$ | <0.09 | >100.0 | >100.0 | — |

| Compound No. | Inhibition of Cholinesterase $I_{50}$ (M) (1) | | | Insecticidal Activity $LD_{50}$ (μg/g) (2) |
|---|---|---|---|---|
| | S (3) | R (4) | R/S (5) | R (4) |
| 50* | $1.1 \times 10^{-6}$ | $5.1 \times 10^{-5}$ | 46.4 | >100 |
| 51 | $4.2 \times 10^{-5}$ | $1.1 \times 10^{-5}$ | 0.3 | 79.8 |
| 57* | $2.3 \times 10^{-6}$ | $7.3 \times 10^{-5}$ | 31.7 | >100 |
| 58 | $1.0 \times 10^{-4}$ | $1.5 \times 10^{-5}$ | 0.2 | 50.0 |
| 59* | $2.3 \times 10^{-6}$ | $5.7 \times 10^{-5}$ | 24.8 | >100 |
| 60 | $1.5 \times 10^{-4}$ | $2.5 \times 10^{-5}$ | 0.2 | 95.0 |
| 63* | $1.0 \times 10^{-6}$ | $1.5 \times 10^{-5}$ | 15.0 | 35.4 |
| 64 | $2.9 \times 10^{-5}$ | $4.4 \times 10^{-6}$ | 0.2 | 28.0 |
| 76* | $1.7 \times 10^{-5}$ | $5.5 \times 10^{-4}$ | 32.3 | 100.0 |
| 77 | $4.5 \times 10^{-4}$ | $2.4 \times 10^{-4}$ | 0.5 | 58.7 |
| 79* | $2.5 \times 10^{-5}$ | $3.0 \times 10^{-4}$ | 12.0 | >100.0 |
| 80 | $>10^{-3}$ | $2.4 \times 10^{-4}$ | <0.2 | 85.2 |
| 81* | $3.8 \times 10^{-6}$ | $1.3 \times 10^{-4}$ | 34.2 | >100.0 |
| 83 | $3.9 \times 10^{-4}$ | $1.8 \times 10^{-4}$ | 0.4 | 30.1 |
| 85 | $1.1 \times 10^{-4}$ | $8.6 \times 10^{-5}$ | 0.8 | 70.7 |
| 86* | $2.1 \times 10^{-6}$ | $6.7 \times 10^{-3}$ | 31.9 | 76.0 |
| 87 | $2.2 \times 10^{-4}$ | $7.4 \times 10^{-5}$ | 0.3 | 61.2 |
| 88* | $7.0 \times 10^{-6}$ | $1.1 \times 10^{-4}$ | 15.7 | 100.0 |
| 89 | $3.8 \times 10^{-4}$ | $8.9 \times 10^{-5}$ | 0.2 | 56.1 |
| 90* | $8.2 \times 10^{-6}$ | $7.9 \times 10^{-5}$ | 9.6 | >100.0 |
| 91 | $4.2 \times 10^{-4}$ | $6.3 \times 10^{-5}$ | 0.2 | 42.6 |
| 92* | $1.7 \times 10^{-5}$ | $3.0 \times 10^{-4}$ | 17.6 | >100.0 |
| 93 | $4.4 \times 10^{-4}$ | $3.5 \times 10^{-4}$ | 0.8 | 80.4 |
| 94 | $10^{-4}$ | $1.9 \times 10^{-4}$ | 0.2 | 70.7 |
| 98* | $4.1 \times 10^{-6}$ | $3.6 \times 10^{-4}$ | 87.8 | >100 |
| 99 | $1.8 \times 10^{-4}$ | $1.2 \times 10^{-5}$ | 0.07 | 58.7 |
| 100* | $3.5 \times 10^{-5}$ | $8.5 \times 10^{-4}$ | 24.3 | 100 |
| 101 | $8.3 \times 10^{-4}$ | $2.2 \times 10^{-4}$ | 0.3 | 50.0 |
| 106* | $9.6 \times 10^{-6}$ | $1.3 \times 10^{-4}$ | 13.5 | 39.9 |
| 107 | $3.9 \times 10^{-4}$ | $8.9 \times 10^{-5}$ | 0.02 | 31.6 |
| 110* | $2.3 \times 10^{-6}$ | $1.7 \times 10^{-4}$ | 73.9 | 54.3 |
| 111 | $3.8 \times 10^{-5}$ | $2.7 \times 10^{-5}$ | 0.7 | 22.7 |
| 135* | $1.0 \times 10^{-5}$ | $3.5 \times 10^{-5}$ | 3.5 | 28.5 |
| 136 | $2.9 \times 10^{-4}$ | $2.6 \times 10^{-5}$ | 0.09 | 21.7 |
| 137 | $9.8 \times 10^{-5}$ | $2.5 \times 10^{-5}$ | 0.3 | 26.0 |

| Compound No. | Inhibition of Cholinesterase $I_{50}$ (M) | | | Insecticidal Activity $_{50}$ (μg/g) | | R/S |
|---|---|---|---|---|---|---|
| | S | R | R/S | S | R | |
| 140* | $1.3 \times 10^{-4}$ | $>10^{-3}(42.5)**$ | >7.6 | 19.0 | >100 | >5.3 |
| 141 | $>10^{-3}(30.4)**$ | $>10^{-3}(43.4)**$ | — | >100 | >100 | — |
| 142 | $>10^{-3}(12.0)**$ | $6.6 \times 10^{-4}$ | <0.6 | >100 | >100 | — |
| 143 | $>10^{-3}(3.3)**$ | $>10^{-3}(46.0)**$ | — | >100 | >100 | — |
| 144 | $>10^{-3}(10.00)**$ | $5.2 \times 10^{-4}$ | <0.5 | >100 | >100 | — |

Marked with ** is the rate of inhibition (%) in $10^{-3}$M

Notes:
(1) 50% inhibition concentration (M)
(2) 50% lethal dosage (μ/g)
(3) Susceptible strain
(4) Resistant strain
(5) Resistant ratio: the ratio of the resistant strain to the susceptible strain, showing the increasing degree of the resistance.

Table 5-1

| Compound | $LD_{50}$ (μg/g) R | Synergistic ratio R/S |
|---|---|---|
| 1* + 2 | 47.0 | 1.4 |
| 1* + 3 | 29.0 | 2.5 |
| 1* + 4 | 35.1 | >2.3 |
| 1* + 5 | 42.9 | 1.1 |
| 1* + 8 | 34.1 | 2.0 |
| 1* + 13 | 13.3 | 3.0 |
| 1* + 17 | 13.7 | 1.6 |
| 1* + 21 | 13.6 | 2.3 |
| 1* + 27 | 19.8 | 3.1 |
| 1* + 31 | 16.3 | 2.7 |
| 1* + 32 | 16.3 | 3.6 |
| 1* + 34 | 32.9 | 1.6 |

Table 5-1-continued

| Compound | LD$_{50}$ (μg/g) R | Synergistic ratio R/S |
|---|---|---|
| 1* + 37 | 17.7 | 2.5 |
| 1* + 42 | 17.7 | 2.8 |
| 1* + 47 | 15.3 | 3.2 |
| 6* + 3 | 21.2 | 3.3 |
| 6* + 8 | 22.5 | 3.1 |
| 6* + 10 | 35.4 | 1.5 |
| 6* + 17 | 9.9 | 2.1 |
| 6* + 21 | 3.8 | 3.6 |
| 6* + 25 | 38.9 | 1.8 |
| 6* + 26 | 14.8 | 4.2 |
| 6* + 27 | 43.8 | 2.8 |
| 6* + 31 | 19.0 | 2.2 |
| 6* + 33 | 15.3 | 3.8 |
| 6* + 34 | 20.5 | 2.7 |
| 6* + 37 | 22.3 | 1.9 |
| 6* + 42 | 20.0 | 2.7 |
| 6* + 47 | 16.3 | 2.9 |
| 24* | 39.4 | — |
| 24* + 3 | 27.4 | 1.8 |
| 24* + 8 | 29.4 | 1.6 |
| 24* + 17 | 8.2 | 2.3 |
| 24* + 21 | 8.2 | 3.2 |
| 24* + 23 | 12.5 | 1.8 |
| 24* + 26 | 12.0 | 4.0 |
| 24* + 31 | 12.5 | 2.7 |
| 24* + 33 | 16.3 | 2.7 |
| 24* + 34 | 30.6 | 1.3 |
| 24* + 37 | 16.3 | 2.4 |
| 24* + 39 | 16.5 | 1.8 |
| 24* + 42 | 19.0 | 2.3 |
| 24* + 44 | 23.5 | 2.1 |
| 24* + 47 | 20.4 | 1.7 |
| 35* | 21.3 | — |
| 35* + 3 | 19.0 | 1.6 |
| 35* + 5 | 15.1 | 1.2 |
| 35* + 8 | 27.0 | 1.1 |
| 35* + 10 | 28.0 | 1.1 |
| 35* + 17 | 7.8 | 1.2 |
| 35* + 21 | 9.6 | 1.5 |
| 35* + 23 | 14.4 | 1.3 |
| 35* + 26 | 10.8 | 2.7 |
| 35* + 37 | 10.0 | 2.3 |
| 35* + 39 | 16.3 | 1.4 |
| 35* + 42 | 12.5 | 2.1 |
| 35* + 44 | 20.4 | 1.4 |
| 40* | 25.0 | — |
| 40* + 3 | 28.8 | 1.3 |
| 40* + 5 | 23.5 | 1.2 |
| 40* + 8 | 29.1 | 1.3 |
| 40* + 10 | 32.6 | 1.1 |
| 40* + 17 | 8.8 | 1.9 |
| 40* + 21 | 8.8 | 2.5 |
| 40* + 24 | 16.5 | 1.2 |
| 40* + 26 | 12.5 | 2.8 |
| 40* + 31 | 15.3 | 1.8 |
| 40* + 33 | 17.7 | 2.0 |
| 40* + 34 | 17.7 | 1.8 |
| 40* + 37 | 9.5 | 2.9 |
| 40* + 39 | 25.0 | 1.0 |
| 40* + 42 | 8.8 | 3.1 |
| 40* + 44 | 22.0 | 1.6 |
| 40* + 47 | 21.7 | 1.3 |
| 32* | 50.0 | — |
| 32* + 8 | 35.4 | 1.6 |
| 32* + 26 | 14.0 | 3.6 |
| 32* + 28 | 27.1 | 2.3 |
| 32* + 37 | 12.5 | 2.9 |
| 32* + 42 | 15.7 | 2.7 |
| 45* | 39.6 | — |
| 45* + 8 | 19.0 | 2.6 |
| 45* + 26 | 10.8 | 4.1 |
| 45* + 28 | 21.7 | 2.6 |
| 45* + 37 | 12.5 | 2.7 |
| 45* + 42 | 16.3 | 2.4 |
| 45* + 51 | 12.5 | 2.1 |
| 49* | 25.0 | — |
| 49* + 3 | 25.0 | 1.4 |
| 49* + 8 | 31.2 | 1.1 |
| 49* + 17 | 11.1 | 1.5 |
| 49* + 21 | 11.7 | 2.1 |
| 49* + 23 | 13.5 | 1.5 |
| 49* + 26 | 14.8 | 2.2 |
| 49* + 37 | 12.5 | 1.4 |
| 49* + 39 | 14.0 | 1.8 |
| 49* + 42 | 14.4 | 1.9 |
| 49* + 44 | 19.0 | 1.9 |
| 75* | 65.8 | — |
| 75* + 3 | 32.8 | 2.0 |
| 75* + 8 | 25.0 | 2.6 |
| 75* + 17 | 13.0 | 1.0 |
| 75* + 21 | 12.5 | 2.5 |
| 75* + 26 | 19.0 | 3.0 |
| 75* + 37 | 25.0 | 1.6 |
| 75* + 42 | 17.7 | 2.6 |
| 81* | >100.0 | — |
| 81* + 3 | 30.2 | >2.5 |
| 81* + 8 | 36.2 | >2.1 |
| 81* + 17 | 10.8 | >2.1 |
| 81* + 21 | 10.7 | >3.1 |
| 81* + 26 | 19.0 | >3.7 |
| 81* + 37 | 14.4 | >3.1 |
| 81* + 42 | 23.1 | >2.3 |
| 126* | 12.5 | — |
| 126* + 8 | 20.4 | 1.0 |
| 126* + 26 | 20.4 | 1.0 |
| 126* + 28 | 12.5 | 1.7 |
| 126* + 37 | 14.7 | 1.1 |
| 126* + 42 | 17.7 | 1.0 |
| 2 + 3 | 53.4 | 1.2 |
| 1* + 2 + 3 | 44.8 | — |
| 1* + 2 + 3 + 4 | 35.4 | — |
| 6* + 26 + 49* | 17.7 | — |

Table 5-2

| Compound No. | Effect of individual compound | Compound No. | | | | | | | | LD$_{50}$ (μg/g) | |
|---|---|---|---|---|---|---|---|---|---|---|---|
| | | 1* 82.8 | 6* 76.6 | 24* 39.4 | 81* >100 | 35* 21.3 | 40* 25.0 | 49* 25.0 | 118* 11.7 | Carbofuran (1) 10.7 | Methomyl (2) 8.2 |
| 50* | >100 | >100 | >100 | 84.2 | >100 | 49.0 | 57.4 | 54.6 | 23.5 | 30.4 | 23.7 |
| 51 | 79.8 | 31.0 | 30.6 | 28.9 | 37.8 | 24.5 | 23.6 | 19.9 | 12.4 | 13.0 | 10.8 |
| 52* | >100 | >100 | >100 | 83.1 | >100 | 84.2 | 89.3 | 64.8 | 30.2 | 31.2 | 33.2 |
| 53 | >100 | 52.3 | 48.3 | 32.1 | 58.1 | 28.3 | 33.1 | 30.3 | 12.1 | 11.8 | 12.3 |
| 54* | >100 | >100 | >100 | 76.4 | >100 | 53.9 | 52.9 | 53.4 | 27.4 | 25.5 | 20.3 |
| 55 | >100 | 50.7 | 43.5 | 36.2 | 57.8 | 22.7 | 26.5 | 20.4 | 10.8 | 10.8 | 10.7 |
| 56 | >100 | 53.2 | 46.5 | 39.5 | 62.0 | 23.6 | 29.7 | 27.0 | 18.4 | 12.3 | 11.9 |
| 57* | >100 | >100 | >100 | 58.4 | >100 | 48.8 | 62.4 | 42.7 | 29.8 | 21.4 | 20.1 |
| 58 | 50 | 16.3 | 15.2 | 11.2 | 19.0 | 14.2 | 11.3 | 11.9 | 8.7 | 8.5 | 8.1 |

Table 5-2-continued

| Compound No. | Effect of individual compound | Compound No. | | | | | | | | $LD_{50}$ ($\mu g/g$) | |
|---|---|---|---|---|---|---|---|---|---|---|---|
| | | 1* | 6* | 24* | 81* | 35* | 40* | 49* | 118* | Carbofuran (1) | Methomyl (2) |
| | | 82.8 | 76.6 | 39.4 | >100 | 21.3 | 25.0 | 25.0 | 11.7 | 10.7 | 8.2 |
| 59* | >100 | >100 | >100 | 63.2 | >100 | 49.6 | 48.8 | 46.7 | 22.4 | 20.5 | 18.9 |
| 60 | 95.0 | 19.9 | 19.4 | 21.3 | 20.4 | 16.8 | 19.5 | 17.5 | 7.8 | 7.6 | 7.3 |
| 61* | >100 | >100 | >100 | 86.2 | >100 | 56.3 | 61.2 | 54.8 | 28.6 | 24.2 | 23.6 |
| 62 | >100 | 77.4 | 63.0 | 41.2 | 77.6 | 28.7 | 36.9 | 33.2 | 16.3 | 14.2 | 13.9 |
| 63* | 35.4 | 63.4 | 58.0 | 47.4 | 89.4 | 48.6 | 53.2 | 43.9 | 20.2 | 19.9 | 18.6 |
| 64 | 28.0 | 13.2 | 12.4 | 12.5 | 18.6 | 11.2 | 10.3 | 10.2 | 7.4 | 8.2 | 7.7 |
| 65* | >100 | >100 | >100 | 84.3 | >100 | 63.2 | 52.2 | 58.3 | 20.2 | 20.2 | 16.8 |
| 66 | >100 | 43.1 | 46.7 | 41.2 | 53.4 | 26.8 | 23.4 | 22.9 | 12.4 | 11.3 | 10.8 |
| 67 | >100 | >100 | >100 | >100 | 62.2 | 59.6 | 57.4 | 24.2 | 22.3 | 22.3 | 22.3 |
| 68 | >100 | 27.4 | 26.3 | 24.5 | 36.7 | 20.4 | 21.7 | 19.8 | 12.2 | 12.1 | 9.8 |
| 69* | >100 | >100 | >100 | >100 | >100 | 57.9 | 60.6 | 58.1 | 23.6 | 23.5 | 20.2 |
| 70 | >100 | 62.5 | 60.4 | 40.4 | 56.8 | 22.3 | 26.7 | 28.0 | 14.0 | 13.2 | 10.4 |
| 71* | >100 | >100 | >100 | 93.7 | >100 | 59.6 | 57.4 | 50.0 | 19.4 | 21.4 | 18.4 |
| 72 | >100 | 53.2 | 46.3 | 28.4 | 38.2 | 26.7 | 24.5 | 25.0 | 12.4 | 12.2 | 10.0 |
| 73* | >100 | >100 | >100 | >100 | >100 | 63.2 | 53.7 | 51.8 | 26.3 | 28.2 | 20.7 |
| 74 | >100 | 70.4 | 72.3 | 43.2 | 63.1 | 40.3 | 26.3 | 20.2 | 13.3 | 12.4 | 10.5 |
| 76* | 100 | 78.4 | 86.9 | 53.2 | >100 | 45.9 | 39.6 | 51.3 | 27.4 | 23.4 | 21.3 |
| 77 | 58.7 | 26.3 | 21.3 | 26.1 | 23.6 | 17.4 | 19.6 | 15.4 | 9.3 | 10.3 | 10.1 |
| 78 | >100 | 34.0 | 24.7 | 27.4 | 25.3 | 18.7 | 20.7 | 18.5 | 12.4 | 10.9 | 9.8 |
| 79* | >100 | >100 | >100 | 74.3 | >100 | 43.2 | 56.2 | 50.4 | 27.0 | 28.1 | 24.4 |
| 80 | 85.2 | 31.3 | 29.6 | 26.0 | 33.2 | 16.3 | 20.3 | 15.2 | 13.3 | 12.4 | 10.4 |
| 81* | >100 | >100 | >100 | 79.9 | >100 | 53.2 | 56.7 | 42.5 | 26.7 | 28.4 | 20.2 |
| 82 | >100 | 58.4 | 63.1 | 43.5 | 75.0 | 26.5 | 25.0 | 23.1 | 10.4 | 12.7 | 7.4 |
| 83 | 30.1 | 24.5 | 20.7 | 18.4 | 23.4 | 17.4 | 18.5 | 13.8 | 7.5 | 9.3 | 8.5 |
| 84 | >100 | 45.2 | 34.4 | 23.5 | 37.6 | 19.4 | 21.7 | 18.5 | 10.9 | 10.3 | 10.1 |
| 85 | 70.7 | 30.4 | 23.7 | 20.4 | 25.6 | 19.4 | 21.4 | 15.7 | 9.7 | 9.5 | 7.9 |
| 86* | 76.0 | 84.5 | 88.7 | 62.3 | >100 | 53.2 | 49.8 | 57.4 | 28.4 | 26.7 | 21.1 |
| 87 | 61.2 | 24.2 | 28.4 | 28.0 | 32.9 | 20.4 | 26.7 | 16.3 | 10.1 | 8.7 | 8.9 |
| 88* | 100 | 89.4 | 86.3 | 62.4 | >100 | 56.4 | 50.2 | 56.9 | 24.3 | 23.2 | 21.0 |
| 89 | 56.1 | 22.3 | 19.9 | 21.0 | 24.2 | 17.4 | 16.8 | 17.7 | 8.4 | 7.8 | 7.6 |
| 90* | >100 | <100 | 87.4 | 65.3 | >100 | 43.7 | 52.0 | 49.7 | 21.3 | 25.2 | 20.0 |
| 91 | 42.6 | 21.3 | 20.1 | 21.7 | 22.3 | 20.4 | 18.7 | 20.3 | 10.1 | 9.8 | 8.6 |
| 92 | >100 | 93.2 | 96.7 | 68.3 | >100 | 56.7 | 56.2 | 43.7 | 28.4 | 26.9 | 19.9 |
| 93 | 80.4 | 26.3 | 31.2 | 25.4 | 40.1 | 21.7 | 23.2 | 20.6 | 12.4 | 10.8 | 8.5 |
| 94 | 70.7 | 21.2 | 20.3 | 24.1 | 30.9 | 18.4 | 19.7 | 18.7 | 9.3 | 10.1 | 7.4 |
| 95 | >100 | 33.4 | 27.9 | 23.0 | 34.8 | 21.1 | 20.7 | 20.0 | 12.2 | 13.2 | 10.4 |
| 96* | >100 | >100 | >100 | 66.7 | >100 | 43.2 | 61.0 | 57.9 | 29.0 | 28.2 | 20.9 |
| 97 | >100 | 42.4 | 38.9 | 33.6 | 51.4 | 37.8 | 34.5 | 40.7 | 17.4 | 16.3 | 12.4 |
| 98* | >100 | >100 | >100 | 86.4 | >100 | 50.9 | 53.2 | 49.7 | 26.8 | 24.3 | 20.2 |
| 99 | 58.7 | 23.4 | 26.7 | 22.5 | 36.8 | 22.5 | 26.3 | 21.4 | 13.2 | 11.5 | 10.2 |
| 100* | 100 | >100 | >100 | 89.7 | >100 | 46.8 | 53.6 | 54.2 | 27.4 | 26.3 | 20.8 |
| 101 | 50.0 | 24.0 | 26.7 | 25.6 | 40.3 | 23.5 | 21.4 | 20.7 | 12.4 | 10.8 | 10.3 |
| 102* | >100 | >100 | >100 | 78.9 | >100 | 46.7 | 51.2 | 56.7 | 27.0 | 30.1 | 23.0 |
| 103 | >100 | 26.7 | 35.2 | 36.7 | 54.2 | 31.2 | 41.0 | 32.1 | 12.3 | 15.9 | 12.2 |
| 104 | >100 | 21.7 | 24.2 | 23.0 | 42.7 | 22.3 | 26.2 | 23.2 | 12.3 | 11.8 | 10.7 |
| 105 | >100 | 23.4 | 34.9 | 34.5 | 66.5 | 32.9 | 34.2 | 45.0 | 13.4 | 14.2 | 11.3 |
| 106* | 39.9 | >100 | >100 | 83.4 | >100 | 49.8 | 55.4 | 39.8 | 32.1 | 38.2 | 34.1 |
| 107 | 31.6 | 16.2 | 14.8 | 14.4 | 25.5 | 16.1 | 11.2 | 10.2 | 10.1 | 9.2 | 8.9 |
| 108* | 0 | 0 | 0 | 0 | 0 | 0 | 0 | 0 | 20.0 | 40.0 | 35.0 |
| 109 | 35.0 | 100 | 100 | 100 | 90.0 | 95.0 | 95.0 | 100 | 90.0 | 95.0 | 90.0 |
| 110* | 0 | 0 | 0 | 0 | 0 | 0 | 0 | 0 | 20.0 | 35.0 | 30.0 |
| 111 | 15.0 | 80.0 | 80.0 | 90.0 | 80.0 | 95.0 | 90.0 | 95.0 | 90.0 | 95.0 | 90.0 |
| 112 | 0 | 0 | 0 | 0 | 0 | 0 | 0 | 0 | 30.00 | 35.0 | 45.0 |
| 113 | 40.0 | 85.0 | 80.0 | 100 | 90.0 | 100 | 95.0 | 90.0 | 95.0 | 90.0 | 85.0 |
| 114 | 15.0 | 70.0 | 85.0 | 95.0 | 95.0 | 95.0 | 100 | 100 | 85.0 | 90.0 | 100 |
| 115 | 10.0 | 85.0 | 85.0 | 90.0 | 95.0 | 95.0 | 100 | 90.0 | 90.0 | 90.0 | 95.0 |
| 116* | 5.0 | 0 | 0 | 5.0 | 0 | 0 | 0 | 5.0 | 20.0 | 45.0 | 30.0 |
| 117 | 35.0 | 100 | 100 | 90.0 | 90.0 | 95.0 | 95.0 | 95.0 | 90.0 | 90.0 | 95.0 |
| 118* | 23.5 | 25.0 | 30.0 | 25.0 | 30.0 | 25.0 | 30.0 | 20.0 | 50.0 | 55.0 | 45.0 |
| 119 | 25.0 | 80.0 | 90.0 | 90.0 | 90.0 | 100 | 95.0 | 90.0 | 90.0 | 95.0 | 90.0 |
| 120 | 30.0 | 100 | 100 | 95.0 | 100 | 100 | 100 | 100 | 55.0 | 95.0 | 95.0 |
| 121 | 15.0 | 70.0 | 72.5 | 92.5 | 90.0 | 95.0 | 100 | 95.0 | 70.0 | 75.0 | 85.0 |
| 122 | 45.0 | 95.0 | 90.0 | 100 | 90.0 | 95.0 | 95.0 | 95.0 | 90.0 | 75.0 | 85.0 |
| 123* | 5.0 | 0 | 0 | 0 | 0 | 0 | 0 | 0 | 40.0 | 35.0 | 35.0 |
| 124 | 5.0 | 80.0 | 80.0 | 85.0 | 90.0 | 100 | 95.0 | 95.0 | 100 | 90.0 | 90.0 |
| 125 | 25.0 | 85.0 | 80.0 | 95.0 | 80.0 | 95.0 | 95.0 | 90.0 | 95.0 | 90.0 | 100 |
| 126* | 15.0 | 0 | 0 | 0 | 0 | 5.0 | 0 | 0 | 25.0 | 30.0 | 35.0 |
| 127 | 35.0 | 70.0 | 75.0 | 75.0 | 95.0 | 90.0 | 90.0 | 95.0 | 90.0 | 95.0 | 95.0 |
| 128 | 45.0 | 85.0 | 85.0 | 85.0 | 70.0 | 100 | 100 | 70.0 | 90.0 | 95.0 | 90.0 |
| 129 | 35.0 | 80.0 | 80.0 | 85.0 | 70.0 | 90.0 | 95.0 | 70.0 | 90.0 | 95.0 | 95.0 |
| 130 | 35.0 | 85.0 | 90.0 | 90.0 | 80.0 | 100 | 100 | 100 | 90.0 | 100 | 100 |
| 131* | 0 | 0 | 0 | 0 | 0 | 0 | 0 | 0 | 35.0 | 35.0 | 40.0 |
| 132 | 40.0 | 80.0 | 85.0 | 95.0 | 70.0 | 95.0 | 100 | 100 | 90.0 | 95.0 | 100 |
| 133* | 16.5 | 32.5 | 33.8 | 35.4 | 40.2 | 31.8 | 38.2 | 27.8 | 15.6 | 14.7 | 12.8 |
| 134 | 28.8 | 11.3 | 12.5 | 11.7 | 16.3 | 10.2 | 10.3 | 7.3 | 8.4 | 8.2 | 7.7 |
| 135* | 28.5 | 45.7 | 56.3 | 46.7 | 63.2 | 46.8 | 40.2 | 46.7 | 16.8 | 17.4 | 18.8 |
| 136 | 21.7 | 18.4 | 15.2 | 10.7 | 16.2 | 18.4 | 15.5 | 17.4 | 10.3 | 12.5 | 10.1 |
| 137 | 26.0 | 16.7 | 14.6 | 15.3 | 16.2 | 13.2 | 16.8 | 16.5 | 9.7 | 8.7 | 8.5 |
| 138* | 25.0 | 56.3 | 57.9 | 46.3 | 58.4 | 42.5 | 38.7 | 34.5 | 16.7 | 18.4 | 13.4 |

Table 5-2-continued

| Compound No. | Effect of individual compound | Compound No. | | | | | | | | LD$_{50}$ ($\mu$g/g) | |
|---|---|---|---|---|---|---|---|---|---|---|---|
| | | 1* | 6* | 24* | 81* | 35* | 40* | 49* | 118* | Carbofuran (1) | Methomyl (2) |
| | | 82.8 | 76.6 | 39.4 | >100 | 21.3 | 25.0 | 25.0 | 11.7 | 10.7 | 8.2 |
| 139 | 32.9 | 13.5 | 14.2 | 11.3 | 19.7 | 13.2 | 14.5 | 8.7 | 7.8 | 7.6 | 7.8 |
| 140* | >100 | >100 | >100 | >100 | >100 | 62.3 | 70.7 | 60.5 | 34.5 | 30.0 | 27.3 |
| 141 | >100 | 29.0 | 28.9 | 30.3 | 42.5 | 23.2 | 24.5 | 23.7 | 22.3 | 11.5 | 9.3 |
| 142 | >100 | 24.6 | 28.2 | 25.0 | 32.7 | 18.4 | 20.3 | 17.2 | 10.3 | 9.8 | 8.0 |
| 143 | >100 | 34.5 | 36.7 | 35.2 | 40.3 | 22.0 | 19.3 | 20.0 | 11.3 | 12.0 | 10.5 |
| 144 | >100 | 25.7 | 22.0 | 26.3 | 34.2 | 21.2 | 18.6 | 16.3 | 9.7 | 10.2 | 9.0 |

(1) 2,3-dihydro-2,2-dimethyl-benzofuran-7-yl-N-methylcarbamate
(2) 1-(methylthio)ethylideneamino-N-methylcarbamate

Test Example 2

The test for insecticidal activity exhibited on resistant green rice leafhoppers (R) were carried out by following the Test Example 1 in various mixing ratio. The results of the test were as shown in Table 6.

Table 6

| Compound No. | mixing ratio (weight ratio) | LD$_{50}$ ($\mu$g/g) | Cooperation coefficient |
|---|---|---|---|
| 1* | | 89.2 | |
| 3 | | 79.1 | |
| 1* + 3 | 3 : 1 | 34.1 | 2.4 |
| | 2 : 1 | 15.3 | 5.3 |
| | 1 : 1 | 25.0 | 3.2 |
| | 1 : 2 | 28.5 | 2.8 |
| | 1 : 3 | 35.4 | 2.3 |
| 1* | | 82.2 | |
| 26 | | 52.2 | |
| 1* + 26 | 3 : 1 | 24.4 | 2.1 |
| | 2 : 1 | 14.4 | 5.1 |
| | 1 : 1 | 10.6 | 5.5 |
| | 1 : 2 | 10.0 | 4.2 |
| | 1 : 3 | 22.8 | 2.6 |
| 6* | | 70.7 | |
| 26 | | 51.2 | |
| 6* + 26 | 3 : 1 | 14.8 | 4.0 |
| | 2 : 1 | 20.4 | 2.9 |
| | 1 : 1 | 14.3 | 4.1 |
| | 1 : 2 | 14.8 | 4.0 |
| | 1 : 3 | 19.1 | 3.1 |

Test Example 3

The insecticides in the form of dust were tested for insecticidal activity. The results of the test were as shown in Tables 7, 8 and 9.

Table 7

| Compound No. | Mortality (%) after 24 hr. | |
|---|---|---|
| | 100 mg Spary | 250 mg Spray |
| 6* | | 10 |
| 8 | | 80 |
| 10 | | 100 |
| 24* | 0 | 20 |
| 26 | 70 | 100 |
| 28 | 60 | 100 |

Table 7-continued

| Compound No. | Mortality (%) after 24 hr. | |
|---|---|---|
| | 100 mg Spary | 250 mg Spray |
| 35* | 0 | 0 |
| 36 | 55 | 80 |
| 37 | 60 | 90 |
| 39 | 50 | 60 |
| 40* | 5 | 15 |
| 41 | 50 | 70 |
| 42 | 70 | 95 |
| 44 | 60 | 80 |
| 45* | 0 | 10 |
| 46 | 45 | 70 |
| 47 | 70 | 100 |

Table 8

| Compound No. | Spray Volume (mg) | Mortality (%) after | | | | |
|---|---|---|---|---|---|---|
| | | 1 | 2 | 4 | 16 | 24 hr. |
| 24* | 100 | | | | | 0 |
| | 250 | | | | | 20 |
| 26 | 100 | | | | | 70 |
| | 250 | | | | | 100 |
| 35* | 100 | | | | | 0 |
| | 250 | | | | | 0 |
| 40* | 100 | | | | | 5 |
| | 250 | | | | | 15 |
| 42 | 100 | | | | | 70 |
| | 250 | | | | | 95 |
| 6* + 42 | 100 | 0 | 10 | 10 | 55 | 55 |
| | 250 | 25 | 55 | 85 | 95 | 95 |
| | 500 | 40 | 75 | 95 | 100 | 100 |
| 24* + 26 | 100 | 30 | 50 | 60 | 90 | 90 |
| | 250 | 60 | 80 | 100 | 100 | 100 |
| | 500 | 70 | 90 | 100 | 100 | 100 |
| 35* + 42 | 100 | 0 | 10 | 10 | 30 | 60 |
| | 250 | 40 | 50 | 60 | 80 | 90 |
| | 500 | 40 | 50 | 70 | 90 | 90 |
| 40* + 26 | 100 | 20 | 30 | 50 | 70 | 70 |
| | 250 | 40 | 60 | 70 | 90 | 100 |
| | 500 | 60 | 80 | 90 | 100 | 100 |
| 40* + 37 | 100 | 0 | 0 | 0 | 15 | 20 |
| | 250 | 30 | 75 | 95 | 100 | 100 |
| | 500 | 70 | 90 | 100 | 100 | 100 |
| 40* + 42 | 100 | 20 | 50 | 70 | 70 | 70 |
| | 250 | 60 | 70 | 80 | 90 | 100 |
| | 500 | 70 | 90 | 100 | 100 | 100 |

Table 9

| Compound No. | Effect of individual compound (RN) | 1 | 6* | 24* | 81* | 35* | 40* | 49* | 118* | death ratio (%) | |
|---|---|---|---|---|---|---|---|---|---|---|---|
| | | | | | | | | | | Carbofuran | Methomyl |
| | | 0 | 0 | 0 | 0 | 0 | 0 | 0 | 23.4 | 40.0 | 35.0 |
| 76* | 0 | 15.0 | 0 | 20.0 | 35.0 | 10.0 | 0 | 0 | 45.0 | 60.0 | 55.0 |
| 77 | 45.0 | 95.0 | 100 | 100 | 80.0 | 100 | 95.0 | 50.0 | 100 | 100 | 100 |
| 79* | 0 | 0 | 0 | 0 | 5.0 | 0 | 10.0 | 0 | 25.0 | 40.0 | |
| 80 | 0 | 65.0 | 60.0 | 57.5 | 60.0 | 65.0 | 55.0 | 15.0 | 70.0 | 85.0 | 75.0 |
| 81* | 0 | 0 | 5.0 | 0 | 10.0 | 15.0 | 20.0 | 0 | 57.5 | 30.0 | 35.0 |
| 82 | 15.0 | 25.0 | 50.0 | 45.0 | 55.0 | 60.0 | 45.0 | 15.0 | 80.0 | 80.0 | 85.0 |
| 83 | 20.0 | 80.0 | 95.0 | 82.5 | 100 | 100 | 82.5 | 50.0. | 95.0 | 100 | 100 |
| 84 | 0 | 0 | 15.0 | 5.0 | 100 | 10.0 | 5.0 | 0 | 67.5 | 55.0 | 70.0 |
| 85 | 25.0 | 50.0 | 45.0 | 35.0 | 80.0 | 75.0 | 60.0 | 0 | 35.0 | 85.0 | 90.0 |
| 92* | 0 | 0 | 0 | 0 | 0 | 10.0 | 5.0 | 0 | 25.0 | 20.0 | 40.0 |

Table 9-continued

| Compound No. | Effect of individual compound (RN) | 1 | 6* | 24* | 81* | 35* | 40* | 49* | 118* | death ratio (%) Carbofuran | Methomyl |
|---|---|---|---|---|---|---|---|---|---|---|---|
| | | 0 | 0 | 0 | 0 | 0 | 0 | 0 | 23.4 | 40.0 | 35.0 |
| 94 | 0 | 80.0 | 85.0 | 95.0 | 95.0 | 95.0 | 85.0 | 35.0 | 95.0 | 90.0 | 100 |

The test for insecticidal activity was performed by the following procedure. A cylinder formed of a metal gauze (20 mesh) and measuring 3 cm in diameter and 20 cm in height was prepared, in which were placed ten green rice leafhoppers of the strain RN and rice seeds. The dust of a test compound (pulverized by means of a shaking pulverizer made by Taira Kosakusho, Ltd.) was applied onto the tube contents at a prescribed rate by spraying from outside the metal gauze by means of a bell-jar duster. The dust of the test compound was prepared uniformly mixing 2 parts of the dust of the individual compound or 1 part each of the dusts of the mixture components (total 2 parts) and 98 parts of a carrier obtained by mixing talc and clay in equal volumes.

Test Example 4

The compounds were tested by following the method of the Test Example 3 but employing a metal gauze having 35 mesh. The results of the test were as shown in Table 10.

Table 10

| Compound No. | Dusting amount (mg) | Death ratio (%) | | | | |
|---|---|---|---|---|---|---|
| | | 1 hr. | 2 hrs. | 4 hrs. | 16 hrs. | 24 hrs. |
| 6* | 100 | 0 | 0 | 0 | 0 | 0 |
| | 250 | 0 | 0 | 0 | 0 | 0 |
| | 500 | 0 | 0 | 0 | 0 | 0 |
| 49* | 100 | 0 | 0 | 0 | 0 | 0 |
| | 250 | 0 | 0 | 0 | 0 | 0 |
| | 500 | 0 | 0 | 0 | 0 | 0 |
| 24* + 42 | 100 | 0 | 0 | 0 | 10 | 10 |
| | 250 | 0 | 5 | 20 | 65 | 85 |
| | 500 | 5 | 10 | 80 | 100 | 100 |
| 24* + 37 | 100 | 0 | 0 | 0 | 0 | 0 |
| | 250 | 0 | 0 | 40 | 95 | 95 |
| | 500 | 10 | 45 | 95 | 100 | 100 |
| 49* + 42 | 100 | 0 | 0 | 0 | 0 | 5 |
| | 250 | 0 | 0 | 5 | 15 | 25 |
| | 500 | 0 | 0 | 15 | 80 | 80 |

Test Example 5

The compounds were tested for insecticidal activity exhibited on sensitive green rice leafhoppers (S), resistant green rice leafhoppers (R) and green rice leafhoppers of the strain of a markedly developed degree of resistance (RN) by following the Test Example 1. The results of the test were as shown in Table 11.

For the comparison, the same test was carried out using a commercially available insecticide (A) having, as the active component, O,O-diethyl-O-2-isopropyl-4-methyl-6-pyrimidinylphosphorothionate and insecticide (B) having, as the active component, O,O-diethyl-O-(-3-oxo-2-phenyl-2-H-pyridazine-6-yl)phosphorothionate, and the results of this test is also shown in Table 11.

Table 11

| Compound No. | Mixing ratio (W/W) | $LD_{50}$ ($\mu g/g$) | | |
|---|---|---|---|---|
| | | S | R | RN |
| 1* | | 3.6 | 89.2 | 178 |
| 6* | | 2.7 | 76.6 | 178 |
| 1* + 21 | 1:1 | 3.9 | 10.9 | 15.3 |
| 49* + (A) | 1:1 | 2.0 | 10.7 | >25.0(note 1) (20%) |
| 24* + (B) | 1:1 | 5.9 | 11.5 | >25.0(note 2) (0%) |

Note 1: The dosage of 25.0 μg/g showed only 20% as death rate of RN.
Note 2: The dosage of 25.0 μg/g showed 0% as death rate of RN.

Test Example 6: (Standard Method)

The compounds were tested for insecticidal activity exhibited on resistant female green rice leafhopper imagos (RN-strain) by following the method of the Test Example 1, the results being as shown in Table 12.

Test Example 7

Mixtures of the carbamate compounds and conventional N-methylcarbamates, as well as two organophosphoric preparations were tested by following the method of the Test Example 3 on resistant green rice leafhoppers of RN-strain.

The test compounds were mixed in a mixing ratio of 1:1:1 (by weight ratio), and the $LD_{50}$ value of the mixtures is for the total amount of dosage of the three compounds.

The test results were as shown in Tables 13 and 14.

Table 12

| Compound No. | Effect of individual compound | Organophosphoric preparation | | | | | | | |
|---|---|---|---|---|---|---|---|---|---|
| | | Malathion 713.5 | MEP >4,000 | PAP 804.3 | MPP >1,000 | Diazinone 62.2 | Ortran 10.9 | Kayaphos 10.9 | Ofnuck 144.5 |
| 3 | 65.8 | 38.0 | >50 | 38.3 | >50 | 39.3 | 19.8 | 14.2 | >50 |
| 8 | 65.8 | 39.0 | >50 | 43.1 | >50 | 37.2 | 21.3 | 13.1 | 48.2 |
| 26 | 51.2 | 36.7 | >50 | 46.3 | >50 | 48.3 | 20.4 | 16.3 | >50 |
| 37 | 49.4 | 35.4 | 48.2 | 35.4 | >50 | >50 | 28.3 | 14.0 | >50 |
| 42 | 35.4 | 31.3 | >50 | 35.8 | >50 | 48.3 | 31.2 | 13.1 | 48.3 |
| 34 | 38.0 | 33.0 | 38.0 | 43.2 | 50 | 37.8 | 21.2 | 15.0 | >50 |

The numerical value given above are those of $LD_{50}$ = μg/g
(The dosage at which 50% of test insects were killed (dosage amount/living body weight)) on resistant green rice leafhoppers of RN-strain.

Table 13

| Compound Name | $LD_{50}$ ($\mu g/g$) |
|---|---|
| Malathion | 713.5 |
| Diazinone | 62.3 |
| Ortran | 10.9 |
| Ofunuck | 144.5 |
| Kayaphos | 10.9 |
| P A P | 804.3 |
| M P P | >1,000 |
| M E P | >4,000 |
| Compound No.1* | 154.5 |
| Compound No.24* | 61.2 |

Table 13-continued

| Compound Name | LD$_{50}$ ($\mu$g/g) |
| --- | --- |
| Compound No.3 | 61.2 |
| Compound No.26 | 50.0 |
| Compound No.3 + Compound No.1* + Malathion | 32.4 |
| Compound No.3 + Compound No.1* + Diazinone | 37.8 |
| Compound No.3 + Compound No.1* + Ortran | 26.8 |
| Compound No.3 + Compound No.1* + Ofunuck | 27.0 |
| Compound No.3 + Compound No.1* + Kayaphos | 19.6 |
| Compound No.3 + Compound No.1* + P A P | 32.4 |
| Compound No.3 + Compound No.1* + M P P | 42.8 |
| Compound No.3 + Compound No.1* + M E P | 34.5 |
| Compound No. 26 + Compound No. 24* + Malathion | 30.6 |
| Compound No. 26 + Compound No. 24* + Diazinone | 40.9 |
| Compound No. 26 + Compound No. 24* + Ortran | 30.6 |
| Compound No. 26 + Compound No. 24 + Ofunuck | 32.9 |
| Compound No. 26 + Compound No. 24* + Kayaphos | 16.5 |
| Compound No. 26 + Compound No. 24* + P A P | 35.4 |
| Compound No. 26 + Compound No. 24* + M P P | 43.4 |
| Compound No. 26 + Compound No. 24* + M E P | 35.4 |

The Table shows the value of LD$_{50}$ = $\mu$g/g on resistant green rice leafhoppers of RN-strain.

Table 14

| Compound name | LD$_{50}$($\mu$g/g) |
| --- | --- |
| I B P | >1,000 |
| Diazinone | 62.2 |
| P A P | 804.3 |
| Malathion | 713.5 |
| Compound No.26 | 50.0 |
| Compound No.37 | 46.7 |
| Compound No.26 + IBP + Diazinone | 50.0 |
| Compound No.37 + IBP + Diazinone | 38.3 |
| Compound No.26 + IBP + PAP | 36.7 |
| Compound No.37 + IBP + PAP | 35.4 |
| Compound No.26 + IBP + Malathion | 28.0 |
| Compound No.37 + IBP + Malathion | 25.0 |
| Compound No.26 + IBP + CUMP | 27.0 |
| Compound No.37 + IBP + CUMP | 26.7 |

The Table shows the value of LD$_{50}$ = $\mu$g/g on resistant green rice leafhoppers of RN-strain.

Test Example 8: (W.H.O. Method)

The compounds were tested for insecticidal activity on female house flies (*Musca domestica*) of the strain resistant to organophosphoric preparations (of the strain occurring in Shin-yumenoshima of Tokyo). The results of the test were as shown in Table 15.

Method for insecticidal test (1) Each test compound was diluted with acetone in proportion to its insecticidal capacity to produce acetone solutions having the desired concentrations.

(2) To the house flies anesthetized with carbon dioxide gas, the solution was locally applied to the rear side of the prothorax at a dose of 1 $\mu$l per head.

(3) The house flies treated were placed in a plastic cup (measuring 7 cm in diameter and 3.5 cm in depth and containing therein two pieces of adsorbent cotton measuring 1 cm$\times$2 cm and impregnated one with an aqueous 5% sugar solution and the other with an aqueous 5% powdered milk solution) and kept in a glasshouse at a constant temperature of 25$\pm$1° C. At the end of 24 hours' standing, a count was taken of the number of house flies that had died by that time. For the determination of LD$_{50}$ (the dosage at which 50% of test insects were killed), a total of 50 female house flies in their adult state were used for each compound. The seven compounds of the present invention indicated in the table which were applied singly showed 0% as death rate of insects when used at a concentration of 1.0%. The value of LD$_{50}$ found for each mixed composition is reported in terms of the dose of organophosphoric preparation with which the test compound was mixed in a ratio of 1:1.

Table 15

| Com-pound No. | Effect of individual compound | Organophosphoric preparation | | | | |
| --- | --- | --- | --- | --- | --- | --- |
| | | Mala-thion 1.0 | Diazi-none 0.63 | MPP 0.48 | MEP 1.5 | PAP 0.90 |
| 3 | >1.0 | 0.37 | 0.09 | 0.20 | 0.67 | 0.53 |
| 8 | >1.0 | 0.34 | 0.23 | 0.18 | 0.72 | 0.41 |
| 26 | >1.0 | 0.11 | 0.08 | 0.13 | 0.15 | 0.08 |
| 37 | >1.0 | 0.34 | 0.09 | 0.18 | 0.20 | 0.12 |
| 42 | >1.0 | 0.33 | 0.69 | 0.39 | 1.7 | 0.62 |
| 13 | >1.0 | 0.31 | 0.33 | 0.23 | 0.92 | 0.31 |

The numerical values given above are those of LD$_{50}$ on resistant house flies of the strain of Shin-yumenoshima.

Test Example 9: (W.H.O. Method)

The compounds were tested for insecticidal activity exhibited on Culex pipiens pallens (Akaieka in Japanese) which were immunized against organophosphoric preparations and which were in their last larval state (of the Amagasaki-strain). The results of the test were as shown in Table 16.

Method for insecticidal test (1) An ethyl alcohol solution of each test compound was diluted with water to varying concentrations in the range of from 0.01 to 1.0 ppm.

(2) A 200-ml portion of each solution of a different concentration was placed in a 300-ml beaker. Then 30 test insects were plunged into the solution and then removed.

(3) The insects removed from the solution were kept in a greenhouse at a constant temperature of 25$\pm$1° C. for 24 hours. At the end of 24 hours of standing, a count was taken of the number of insects that had died by that time.

The test described above was repeated twice or thrice. The seven compounds of the present invention indicated in the table which were applied singly showed 0% as death rate of insects when used at a concentration of 1.0 ppm. The value of LD$_{50}$ found for each mixed composition is reported in terms of the dose of organophosphoric preparation with which the test compound was mixed in a ratio of 1:1.

Table 16

| com-pound No. | Effect of compound used singly | Organosphosphoric preparation | | | | |
| --- | --- | --- | --- | --- | --- | --- |
| | | Mala-thion 0.31 | Diazi-none 0.31 | MPP 0.10 | MEP 0.18 | PAP 0.16 |
| 3 | >1.0 | 0.11 | 0.15 | 0.08 | 0.06 | 0.08 |
| 8 | >1.0 | 0.21 | 0.17 | 0.08 | 0.07 | 0.08 |
| 26 | >1.0 | 0.18 | 0.15 | 0.08 | 0.07 | 0.07 |
| 37 | >1.0 | 0.18 | 0.23 | 0.09 | 0.07 | 0.07 |
| 42 | >1.0 | 0.30 | 0.28 | 0.09 | 0.20 | 0.09 |
| 83 | >1.0 | 0.18 | 0.13 | 0.13 | 0.10 | 0.09 |

The numerical values given above are those of LD$_{50}$ on resistant culex pipiens pallens.

Test Example 10: (Standard Method)

The compounds were tested for acaricidal activity exhibited toward citrus red mites (*Panonychus citri* McGregor) immunized from Dimethoate. In Petri dishes 9 cm in diameter, a pure agar solution (1.5% in concentration) was allowed to set. Then leaf discs cut off young leaves of tangerines of species Onshu were placed on the agar in said Petri dishes, four in each dish. About five citrus red mites (male mixed) were inoculated to each leaf disc. Then, a test compound prepared in the form of solution was uniformly applied with a miniature spray at a rate of 1 ml per dish. The Petri dishes were left to stand in a greenhouse at a constant temperature of 25° C. for 24 hours. At the end of this standing, a count was taken of the number of insects which had died by that time. The results were as shown in Table 17.

Table 17

| Compound tested | Concentration (ppm) | Mortality (%) |
| --- | --- | --- |
| 3 + dimethoate | 250 + 250 | 100 |
| 8 + dimethoate | 250 + 250 | 100 |
| 26 + dimethoate | 250 + 250 | 100 |
| 37 + dimethoate | 250 + 250 | 100 |
| 42 + dimethoate | 250 + 250 | 95 |
| 51 + dimethoate | 250 + 250 | 95 |
| 50 + dimethoate | 250 + 250 | 95 |
| 26 | 250 | 85 |
| 51 | 250 | 80 |
| 50 | 250 | 70 |
| dimethoate | 250 | 40 |
| Control plot (no treatment) | — | 0 |

Test Example 11: (Test for Toxicity)

Since the test compounds were insoluble in water, a given test compound was converted into a 1.5% suspension using 0.5% traganth gum. Different amounts of the suspension were injected into the stomaches of test mice with a metal tube. For the test, male mice of the species ddY were used.

The results of the Test were as shown in Table 18.

Table 18

| Compound No. | Ratio (W/W) | $LD_{50}$(mg/kg) after one weak |
| --- | --- | --- |
| 3 |  | 1,130 |
| 1* |  | 210 |
| 17 |  | 30–300[1] |
| 15* |  | 87 |
| 21 |  | 300 |
| 19* |  | 54 |
| 120 |  | 30–300[1] |
| 118* |  | 15–63 |
| 24* + 26 | (2:) | 590 |
| 24* + 26 | (1:1) | 506 |
| 24* + 37 | (2:1) | 272 |
| 24* + 37 | (1:1) | 393 |
| 35* + 37 | (1:1) | 135 |

[1]The death rate at 30 mg/kg w as 0% and the death rate at 300 mg/kg was 100%.

What is claimed is:

1. An insecticidal composition containing as the effective agent a synergistic mixture of:
   A. a N-n-propylcarbamate selected from the group consisting of 3-methylphenyl N-n-propylcarbamate; 3,4-dimethylphenyl N-n-propylcarbamate and 3,5-dimethylphenyl N-n-propylcarbamate; and
   B. a N-methylcarbamate selected from the group consisting of 3-methylphenyl N-methylcarbamate; 3,4-dimethylphenyl N-methylcarbamate; 3,5-dimethylphenyl N-methylcarbamate; 2-i-propylphenyl N-methylcarbamate; 2-sec-butylphenyl N-methylcarbamate; 3-t-butylphenyl N-methylcarbamate; 3-methyl-5-i-propylphenyl N-methylcarbamate; 2-chlorophenyl N-methylcarbamate; 2-i-propoxyphenyl N-methylcarbamate and naphthyl N-methylcarbamate; the weight ratio of A to B being within the range of 0.5:1 to 2:1.

2. The composition of claim 1 wherein (A) is 3-methylphenyl-N-n-propyl carbamate.

3. The composition of claim 1 wherein (A) is 3,4-dimethylphenyl-N-n-propyl carbamate.

4. The composition of claim 1 wherein (A) is 3-methylphenyl-N-n-propyl carbamate and (B) is 3-methylphenyl-N-methyl carbamate.

5. The composition of claim 1 wherein (A) is 3-methylphenyl-N-n-propyl carbamate and (B) is 2-sec-butylphenyl-N-methyl carbamate.

6. The composition of claim 1 wherein (A) is 3-methylphenyl-N-n-propyl carbamate and (B) is 3,5-dimethylphenyl-N-methyl carbamate.

7. The composition of claim 1 wherein (A) is 3-methylphenyl-N-n-propyl carbamate and (B) is naphthyl-N-methyl carbamate.

8. A method of killing green rice leafhoppers in the field which comprises applying to said field the composition of claim 1 in an insecticidally effective amount.

9. The method of claim 8 in which said amount is 100 to 300 g of said mixture per 10 ares.

10. The method of claim 8 wherein said mixture consists of 3-methylphenyl-N-n-propyl carbamate and a N-methyl carbamate of group (B).

11. The method of claim 10 wherein said N-methyl carbamate of group (B) is 3-methylphenyl-N-methyl carbamate.

12. The method of claim 10 wherein said N-methyl carbamate of group (B) is 3,4-dimethylphenyl-N-methyl carbamate.

13. The method of claim 10 wherein said N-methyl carbamate of Group (B) is 2-sec-butyl-phenyl-N-methyl carbamate.

* * * * *